(12) United States Patent
Parchment et al.

(10) Patent No.: US 8,709,379 B2
(45) Date of Patent: Apr. 29, 2014

(54) LIPOSOMAL NANOPARTICLES AND OTHER FORMULATIONS OF FENRETINIDE FOR USE IN THERAPY AND DRUG DELIVERY

(75) Inventors: Ralph E. Parchment, Hagerstown, MD (US); Bhaskara R. Jasti, Stockton, CA (US); Ramesh R. Boinpally, Broomfield, CO (US); Stephen E. Rose, Flushing, MI (US); Earle T. Holsapple, Grosse Pointe Farms, MI (US)

(73) Assignee: Scitech Development, LLC, Grosse Pointe Farms, MI (US)

( * ) Notice: Subject to any disclaimer, the term of this patent is extended or adjusted under 35 U.S.C. 154(b) by 1045 days.

(21) Appl. No.: 12/301,587

(22) PCT Filed: Mar. 29, 2007

(86) PCT No.: PCT/US2007/065556
§ 371 (c)(1),
(2), (4) Date: Dec. 17, 2009

(87) PCT Pub. No.: WO2007/115134
PCT Pub. Date: Oct. 11, 2007

(65) Prior Publication Data
US 2012/0093718 A1 Apr. 19, 2012

Related U.S. Application Data

(60) Provisional application No. 60/786,838, filed on Mar. 29, 2006.

(51) Int. Cl.
A61K 51/00 (2006.01)
(52) U.S. Cl.
USPC ............ 424/1.29; 424/502; 424/9.3; 424/9.6; 264/9; 514/613; 977/773; 977/797; 977/906
(58) Field of Classification Search
None
See application file for complete search history.

(56) References Cited

U.S. PATENT DOCUMENTS

| 4,323,581 | A | 4/1982 | Gander |
| 4,874,795 | A | 10/1989 | Yesair |
| 5,091,188 | A | 2/1992 | Haynes |
| 5,269,979 | A | 12/1993 | Fountain |
| 5,314,921 | A | 5/1994 | Yesair |
| 5,741,822 | A | 4/1998 | Yesair |
| 5,891,466 | A | 4/1999 | Yesair |
| 5,895,659 | A | 4/1999 | Luddecke et al. |
| 5,972,911 | A | 10/1999 | Yesair |
| 5,997,888 | A | 12/1999 | Weder et al. |
| 6,017,549 | A | 1/2000 | Knight et al. |
| 6,334,999 | B1 | 1/2002 | Gilbert et al. |
| 6,352,844 | B1 | 3/2002 | Maurer et al. |
| 6,443,898 | B1 * | 9/2002 | Unger et al. .................. 600/458 |
| 6,565,886 | B1 | 5/2003 | Simonnet et al. |
| 6,780,430 | B2 | 8/2004 | Yoo et al. |
| 6,908,625 | B2 | 6/2005 | Lee et al. |
| 7,081,253 | B2 | 7/2006 | Supersaxo et al. |
| 7,169,819 | B2 | 1/2007 | Gupta et al. |
| 7,407,779 | B2 | 8/2008 | Yesair et al. |
| 2002/0183394 | A1 | 12/2002 | Gupta et al. |
| 2003/0180719 | A1 * | 9/2003 | Herget et al. ..................... 435/5 |
| 2005/0106216 | A1 | 5/2005 | Maurer et al. |
| 2005/0287180 | A1 * | 12/2005 | Chen ............................ 424/400 |
| 2007/0134276 | A1 | 6/2007 | Menegatti et al. |
| 2007/0275048 | A1 | 11/2007 | Liu et al. |
| 2008/0269341 | A1 | 10/2008 | Radzioch et al. |

FOREIGN PATENT DOCUMENTS

| CA | 2667091 A1 | 6/2007 |
| JP | 2008127327 A | 6/2008 |
| PL | 159239 A1 | 2/1990 |
| WO | 8906977 A1 | 8/1989 |
| WO | 2005/039532 A1 | 5/2005 |
| WO | 2005120469 A1 | 12/2005 |

OTHER PUBLICATIONS

Takahashi et al., Biol. Pharm. Bull. 26:1060-1063, 2003 (cited as "A" reference).
Supplemental European Search Report and Opinion, EP07759747, dated Jan. 24, 2013.

* cited by examiner

*Primary Examiner* — Suzanne Ziska
(74) *Attorney, Agent, or Firm* — Browdy and Neimark, PLLC

(57) ABSTRACT

Formulations of neutral retinoids, in particular fenretinide (HPR) in the form of lipid nanoparticles, solid dispersions and emulsions are disclosed. These compositions are used to treat diseases that are amenable to treatment by HPR, such as neoplastic diseases by achieving higher and more prolonged concentrations of HPR in the subject. The key steps for preparing lipid nanovesicles of HPR include mixing and sonication, sterile filtration, without or without lyophilization for long-term stable storage, and employ processes and materials that are scalable from the laboratory to the manufacturing level. The formulation are suitable for injection into human or animal patients without causing allergic or hypersensitivity responses by avoiding chemical surfactants and animal sources of phospholipids in their manufacture.

36 Claims, 9 Drawing Sheets myristoyl
myristelaidoyl (C14)    di-myristoyl (C14)    di-myristoyl (C14)    di-myristoyl (C14)

myristoyl (C14)
petroselinoyl (C18)    di-myristoyl (C14)    myristoyl:
myristoleoyl (C14)    di-myristoyl (C14)

LIPOSOMAL NANOPARTICLES AND OTHER FORMULATIONS OF FENRETINIDE FOR USE IN THERAPY AND DRUG DELIVERY

BACKGROUND OF THE INVENTION

1. Field of the Invention

The invention in the field of pharmaceutical science and biomedicine relates to novel formulations of fenretinide (N-4-hydroxyphenylretinamide) in the form of lipid nanoparticles, solid dispersions and emulsions that avoid undesirable components that cause hypersensitivity reactions.

2. Description of the Background Art

Fenretinide (4-hydroxyphenyl-retinamide, abbreviated as HPR or 4-HPR, each of which is used interchangeably herein)) is a synthetic Vitamin A analog of Formula 1, below.

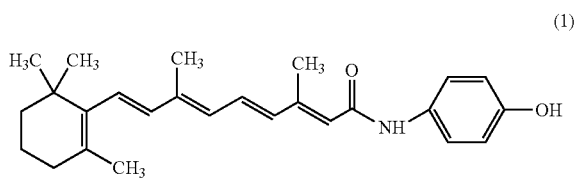 [SMILES: CC1=C(/C=C/C(C)=C/C=C/C(C)=C/C(=O)Nc2ccc(O)cc2)C(C)(C)CCC1]

(1)

HPR was initially developed as a less toxic, better-tolerated amide analog of retinoic acids for chemoprevention of cancer. Trials of HPR as a chemopreventive agent for breast cancer have been disappointing, although it was active in actinic keratosis (Moglia, D et al., 1996, *Cancer Lett* 110:87-91) a precursor condition to squamous cell carcinoma of the skin.

More recent studies showed that micromolar concentrations of HPR, acting independently of retinoid receptors RAR or RXR, induced apoptosis in human tumor cell lines. HPR had a favorable safety profile after parenteral administration. A dose finding study in animals evaluated 100 to 1800 mg HPR/kg/day administered IP for 21 days; the agent was in a suspension in Cremophor®-polyethylene glycol-water (8:10:82) and identified a mouse $LD_{10}$ (lethal dose in 10% of the animals) of 217 mg/kg (651 mg/m²) (Sani, B P et al., 1983, *Toxicol Appl Pharmacol* 70:228-235). A subsequent toxicity study of this dosage form and regimen in Swiss mice and Sprague-Dawley rats revealed lethality and liver and bone marrow toxicity at the $LD_{50}$ but not at the ½$LD_{10}$ or $LD_{10}$. Thus, daily doses as high as ~600 mg/m² for 21 days were well tolerated in rodents. Clinical trials of chronic, low dose oral HPR in high-risk breast cancer patients confirmed that it was well tolerated and without cumulative dose toxicity.

The National Cancer Institute (NCI), interested in exploring higher doses of HPR as a cytotoxic agent for chemotherapy of advanced solid tumors, acquired the rights to this compound for cancer chemotherapy indications as well as the entire supply of clinical grade HPR.

Since the mid-1970s, oral HPR has been studied in animal models of cancer chemoprevention (Moon, R C et al. (1979) *Cancer Res* 39:1339-46; Moon, R C et al. (1982) *Carcinogenesis* 3:1469-72; Pollard, M et al., (1991) *Cancer Lett* 59:159-63; Welsch, C W et al., (1983) *Carcinogenesis* 4:1185-87; Chan, L et al., (1997) *Leuk Lymphoma* 25:271-80) and in human tumor xenograft models of therapy (Dowlatshahi, K et al., (1989) *Canc Lett* 47:187-92; Pienta, K J et al. (1993) *Cancer Res* 53:224-6). HPR was administered in the food or by gavage in a corn oil-ethanol suspension at daily doses from 300-1200 mg/kg/day (0.7-3 mmol/kg) though these studies did not evaluate pharmacokinetics. In separate pharmacokinetic studies, oral doses of 25 and 125 mg/kg/day for 10 days achieved plasma levels of 80 and 260 ng/mL measured 3 hrs after the last dose (Kenel, M F et al., (1988) *Teratog Carcinog Mutagen* 8:1-11). There was a similar increase in the level of the primary metabolite "MPR," the 4-hydroxymethyl derivative of HPR.

An important and perhaps overlooked finding in this study was that an additional 6.5-fold increase in daily dose (from 125 to 800 mg/kg/day) failed to achieve additional increases in plasma HPR (260 and 315 ng/mL) or in the MPR metabolite (60 and 60 ng/mL), suggesting an upper limit on achievable systemic levels using the corn oil-based oral formulation. Such an upper limit severely limits the usefulness of HPR as a chemotherapeutic because plasma concentrations cannot reach cytotoxic levels even if the dose is escalated well-above chemoprevention levels. Thus, one objective of the present inventors was to develop formulations and dose regimens s that would overcome these limitations.

Retinoic acids are soluble in aqueous solvents and can be entrapped inside lipid vesicles. In contrast, HPR and other neutral retinoids exhibit very low water solubility and high octanol:water partition coefficients. Based on these properties, earlier formulation studies by some of the present inventors explored two formulation strategies (i) a protective polymer interface that gradually released HPR as it hydrolyzes, and (ii) solubilizing HPR in water soluble (amphipathic) lipid vesicles or emulsions to take advantage of its natural affinity for lipid membranes.

Protective polymer interfaces used block co-polymers and solid dispersion technology. In the latter, drug solubility is increased by disrupting the crystal structure of the drug by solid-state dispersion into hydrophilic carrier molecules, which replace the drug molecule in the crystal lattice. A key discovery for reducing particle size and increasing dissolution rate involved eutectic mixtures of poorly soluble drugs with physiologically inert carriers such as urea to avoid aggregation and agglomeration in the powder state. This approach evolved into the use of a solid solution in which a drug is molecularly dispersed in a soluble carrier (Chiou, W L et al. (1971) *J Pharm Sci* 60:1569-71; Chiou, W L (1977) *J Pharm Sci* 66:989-91).

The highly investigational nature of newer formulation technologies such as block co-polymer and solid dispersion is a drawback due to (i) the slowing of the time-to clinic as compared to liposomal formulations and (ii) the risk of unanticipated safety problems of excipients.

The minimum HPR exposure level required to inhibit human tumor cell lines in vitro by at least 50-90% is 10 µM for 72 hours as discovered in the following model systems: clonogenic assays of fresh biopsy specimens (Meyskens, F L et al. (1983) *Int J Canc* 32:295-99); neuroblastoma cell lines (Mariotti, A et al., (1994) *J Natl Canc Inst* 86:1245-47); small cell lung carcinoma (SCLC) (Kalemkerian, G P et al., (1995) *J Natl Cance Inst* 87:1674-80); prostate carcinoma (Pienta, K et al., supra; Hsieh, T C et al., (1995) *Biochem Mol Biol Int* 37:499-506); breast carcinoma (Marth, C et al., (1985) *J Natl Cancer Inst* 75:871-875); and cervical cancer (Oridate, N. et al., (1995) *J Cell Biochem Suppl* 23:80-86).

One goal of the present inventors was the discovery of improved compositions and methods for treating pancreatic cancer. Despite its relatively lower incidence, pancreatic cancer has become the fourth leading cause of cancer related deaths (preceded by lung, breast/prostate and colorectal cancer) among both male and female adults in the United States with an estimated 28,200 deaths in 2000 (Greenlee, R T et al., (2000) *CA Cancer J Clin* 50:7-33). No effective method of early diagnosis of this disease is presently available, so pancreatic cancer is commonly diagnosed late in its natural history. It is highly resistant to conventional therapies such as surgical resection or chemotherapy with the nucleoside analog gemcitabine (Gemzar®). Survival is usually 5-9 months. Mortality rates essentially equal disease incidence. Gemcitabine is currently the first-line treatment for patients with locally advanced (nonresectable Stage II or Stage III) or metastatic (Stage IV) adenocarcinoma of the pancreas. Several drugs (Irinotecan, oxaliplatin, docetaxel, etc.) are being studied in combination with gemcitabine. F. Patterson et al., 2001, *Pancreas.* 23:273-9) reported that retinoic acid enhanced the cytotoxic effects of gemcitabine and cisplatin in pancreatic adenocarcinoma cells.

The present inventors' results on xenografts of Bx-PC3 pancreatic tumors revealed activity of HPR, administered intravenously (IV) in a preclinical model. Although oral HPR is in Phase II clinical trials, this dosage form failed to achieve target plasma levels in a Phase I trial, motivating the present inventors to develop new IV formulations. In studies conducted by some of the present inventors and colleagues (Vaishampayan, U et al., 2005, *Invest. New Drugs* 23:179-85), HPR levels in renal cell carcinoma (RCC) biopsies from three patients treated with oral HPR were measured and found to be below those required to induce human tumor cell apoptosis in vitro, which was consistent with the minimal or negative clinical efficacy in this trial (several patients with stable disease but no remissions). Kalemkerian et al. reported moderate effectiveness of HPR in treatment of SCLC patients noted as stable disease in 30% of advanced patients, despite suboptimal plasma concentrations. The foregoing studies point to the significant medical and commercial need for an effective IV dosage form of HPR and methods using this formulation for treatment of pancreatic cancer, RCC and other forms of cancer that overcomes the problem arising from limited blood levels due to poor and limited absorption of orally administered HPR.

Lipid-Based and Polymer-Based Formulations

Parenteral emulsions are finding increasing use as carriers for drugs because of their ability to incorporate drugs into their innermost phase, thus minimizing or bypassing solubility and stability constraints (Andreu, A et al., (1992) *Ann Pharmacother* 26:127-8; Singh, M et al., (1986) *J Parenter Sci Technol* 40:34-41; Lundberg, B. (1994) *J Pharm Sci* 83:72-5; Prankerd, R J et al., (1988) *J Parenter Sci Technol* 42:76-81; Benita, S et al., (1993) *J Pharm Sci* 82:1069-79). Examples of emulsion formulations include the drugs penclomedine, a practically insoluble antitumor agent (Prankerd et al., supra), taxol (Tarr, B D et al., (1987) *Pharm Res* 4:162-65), diazepam (Levy, MY et al. (1989) *Pharm Res* 6:510-516; Levy, MY et al., (1991) *J Parenter Sci Technol* 45:101-7), and propofol (Han, J et al., (2001) *Int J Pharm* 215:207-20).

Liposomes can be customized to modify drug release and (a) target drugs to the reticulo-endothelial system (RES), (b) avoid drug uptake by the RES, and (c) target tumors or other specific tissue sites. Apart from solving the solubility problem, liposomal preparations may achieve target specific drug delivery, prolong the duration of action, reduce the toxicity and thus improve the therapeutic index. For example, doxorubicin in liposomes was found to be 100-times more effective than free drug against liver metastasis of the M5076 tumor (Mayhew, E et at. (1983) *Cancer Drug Deliv* 1:43-58; Mayhew, E et al. (1985) *Prog Clin Biol Res* 172B:301-10). Liposomal encapsulation of amphotericin B, a potent, but extremely toxic, antifungal drug, resulted in an effective product with reduced toxicity. The potential of liposomes and related systems for drug delivery has been realized in several FDA approved intravenous liposomal and lipid-complexed products: Amphotericin B (ABELCET®, Amphotec®, and AmBiosome®), Doxorubicin (Doxil®, Caelyx®), and Daunorubicin (Daunoxome®). For a disease that involve the RES (e.g., leishmaniasis, or a case in which a liposomal system needs to be made tumoricidal by attaching tumor-specific antibodies, a conventional liposome that is "visible" to fixed tissue macrophages is preferable. In contrast, in another context—artificial blood using hemosomes—lipid vesicles must be "invisible" and avoid RES recognition.

One of the present inventors, R. R. Boinpally, and his colleagues identified several variables in preparation of lipid vesicles that enhance delivery to tissues outside the RES (Gopi N et al., 2002, *J Colloid Interface Sci.* 251:360-65; Gopinath, D et al., 2001, *Arzneimittelforschung* 51:924-30; Gopinath, D et al., 2002, *Int J Pharm* 246:187-97; Boinpally R et al., 2001, *J Contr Rel Ann Symp Suppt*; Boinpally R, et al., 2001, *AAPS Pharm Sci Ann Mtg Suppl* 3(3).

Although more soluble retinoic acid drugs like Tretinoin and Iso-tretinoin are available as parenteral dosage forms, and even as encapsulated lipid products (as well as creams and gels), parenteral dosage forms for poorly soluble, neutral retinoid compounds like HPR have never been approved by the FDA, despite a large number of available analogs and numerous reports about their promising anti-cancer potential (Douer D et al., (2000) in *ASCO* Abstr 538; Douer, D et al., 2001, *Blood* 97:73-80).

Studies by the present inventors' laboratories showed that the natural solubility of HPR in aqueous buffer like phosphate buffered saline at pH 7.4 is <1 µg/ml. Although the compound is readily soluble in ethanol, this solvent solubility was not maintained when an ethanol solution of HPR was mixed into aqueous buffered systems, like physiological solutions, and in fact, even when the ethanol content of an aqueous solution of HPR was as high as 20%, the HPR solubility only reached approximately 1-2 µg/ml. Inclusion physiological proteins found in human blood plasma like high density lipoprotein, retinol binding protein, albumin, and al-acid-glycoprotein did not increase HPR solubility to therapeutic levels either, as shown in Table 1, below.

TABLE 1

Maximum Solubility of HPR in Physiological Conditions

| Aqueous System | Additive | Maximum HPR Solubility |
|---|---|---|
| Phosphate buffered saline, (PBS), pH 7.4 | None | Less than 1 µg/ml |
| | Ethanol to 20% of volume | 1-2 µg/ml |
| | High density lipoprotein, 0.2 g/L | 1.5-3 µg/ml |
| | Retinol binding protein, 0.05 g/L | <1 µg/ml |
| | Albumin, 50 g/L | 7-8 µg/ml |
| | α1-acid-glycoprotein, 1 g/L | 1-2 µg/ml |

Related subject matter is described in the following U.S. patents and patent publications of B. J. Maurer and colleagues: U.S. Pat. Nos. 6,352,844 and 6,368,831; U.S. Patent publications, 2005/010167, 2005/0106216, 2005/0187186, 2005/0271707, and 2006/0008508. U.S. Pub. 2002/0183394 and U.S. Pat. No. 7,169,819 (Gupta et al.) disclose of methods of preparing liposomal compositions of HPR and/or other retinoids, liposomal HPR compositions prepared by such methods, and use of such compositions in the treatment of diseases, such as breast cancer. The compositions and methods are distinct from those of the present invention. U.S. Pat publication 2002/0143062 of Lopez-Berestain et al. discloses a pharmaceutical composition for parenteral delivery, that comprises a retinide such as HPR in combination with a solvent capable of dispersing or solubilizing the retinide. The solvent comprises an alcohol, such as ethanol, in combination with an alkoxylated castor oil, such as Cremophor®-EL, or in an emulsion composed of HPR and a lipid dispersed in an aqueous phase, a stabilizing amount of a non-ionic surfactant, optionally a solvent, and optionally an isotonic agent. In addition, a method of use in the treatment of hyperproliferative disorders, such as cancers is described. These compositions and formulations are distinct from the those of the present invention.

To summarize, the clinical potential of HPR as a chemotherapeutic agent has never been realized because existing pharmaceutical technology is limited to oral HPR formulations that cannot achieve therapeutic plasma concentrations. There is thus a need in the art for IV or other parenteral dosage forms of HPR that circumvent these problems and achieve plasma levels adequate to effect cancer cell apoptosis and other clinically desirable effects.

The present formulations, particularly those for intravenous administration of neutral retinoids such as HPR represents the clinical introduction of an appropriate dosage form that can achieve low micromolar concentrations for a "first-in-class retinoid" that induces apoptosis (via pathways independent of RAR/RXR) and has demonstrated efficacy in human tumor models. The present formulations thus have substantial market advantages over those of the prior art and offer clinicians well-tolerated products for treatment of various diseases, including pancreatic cancer and other solid tumors.

SUMMARY OF THE INVENTION

Earlier findings of the present inventors and others pointed to the need for parenteral formulations to realize the full therapeutic potential of HPR and other neutral retinoids to increase the natural water solubility of HPR in order to deliver higher doses into the body via routes other than oral, such as intravenous (IV) or other injectable routes, via inhalation using aerosolized materials, application to the skin as a cream or ointment, etc. In the case of IV therapy, because physiological concentrations of plasma proteins did not increase HPR aqueous solubility substantially, a requirement for pharmaceutical preparations that could maintain higher than natural solubility of HPR in the blood after administration via intravenous or intraarterial routes became evident. Moreover, the present inventors realized the importance of making parenteral formulations composed of pharmaceutical ingredients that are very well tolerated by humans and other mammals and do not cause hypersensitivty or other types of allergic reactions, and can be administered without the need for treatment with co-medications like antihistamines and steroids to block such allergic reactions, or to otherwise provide protections against expected reactions. The formulations described herein, such as the free-flowing lipid nanosystems, provide very high solubility of HPR without the use of allergenic materials like egg lecithins, detergents and other surfactants such as Cremphor EL® that are commonly used in lipid-based formulations and with drugs having low water solubility, including HPR formulations in the prior art.

The present invention is directed to novel formulations of neutral retinoids, preferably HPR, and method of using these formulations to achieve several different objectives:

1. Intravenous (IV) administration of sufficiently high doses of HPR formulated as lipid nanovesicles (a category of liposomes) to treat any form of cancer that is sensitive to HPR;
2. Topical administration of HPR formulated as nanovesicles in a topical formulation to treat precancerous lesions of the skin, such as actinic keratosis, and squamous cell carcinoma (SCC) of the skin.
3. IV administration of HPR lipid nanovesicles which accumulate selectively in the pancreas to treat pancreatic cancer either directly or by delivering another drug or agent (or combination of agents) that is known to be effective against pancreatic cancer, e.g., gemcitabine.
4. Exploitation of the pancreatic accumulation of HPR lipid nanovesicles to treat non-malignant pancreatic disease either directly or by including in such nanovesicles a "payload" comprising either a lipid-based or aqueous drug or agent that can treat such disease.

The latter two embodiments are based on the inventors' recognition and conception that one active pharmaceutical ingredient, namely HPR, can be exploited to deliver additional active ingredients to a specific site in the body, namely the pancreas, to achieve combination therapy.

As noted above and further exemplified herein, tissue distribution studies revealed preferential accumulation of HPR in pancreas over plasma following its oral administration and higher accumulation after IV injection of a lipid vesicle system.

In view of the excellent safety profile of HPR and the potential benefit of its combination with Gemcitabine or other drugs that act on pancreatic cancer (or non-neoplastic pancreatic tissue), the inventors conceived of the use of HPR lipid nanovesicles as delivery systems for such drugs. A nanoparticulate lipid vesicle system serves as a IV vehicle to deliver a combination of a HPR (or any other water insoluble neutral retinoid) and a water soluble agent, such as an anticancer drug, to pancreas (and to other particular tissues) improves the therapeutic outcome.

Existing methods of drug targeting rely on chemical and/or biological targeting agents (pharmacologically "inactive") to target an active agent to a specific site in the body. The concept of utilizing one of the combination agents for systemic administration and targeting of the other in combination therapy to attain synergistic actions is new and particular useful in the treatment of cancer, such as pancreatic cancer.

In a preferred embodiment the HPR lipid nanovesicles of the invention are used to improve efficacy of pancreatic cancer chemotherapy by acting in concert with Gemcitabine, in fact delivering Gemcitabine to the tumor site in the pancreas. Such a combination is expected to be more effective than Gemcitabine alone in a conventional formulation because of (a) additive synergistic actions of the drug combination drugs and (b) the targeting effect, which may be exploited to attain a higher delivered dose.

The present invention is directed to an intravenous preparation of HPR and represents the clinical introduction of an appropriate dosage form for a first-in-class retinoid analog that induces apoptosis via RAR/RXR—independent pathways at low µM concentrations, and has demonstrated efficacy in a large number of human tumor models.

The underlying conception of introducing parenteral, preferably intravenous or topical, HPR is that its clinical potential as a chemotherapeutic agent has never been realized because existing pharmaceutical technology for administering HPR depends upon oral formulations of the drug that cannot achieve therapeutic plasma concentrations. The present invention overcomes these limitations with intravenous/parenteral liposomal dosage form, more specifically a lipid nanoparticle (or nanovesicle—which terms are used interchangeably herein) that achieve HPR plasma levels associated with cancer cell apoptosis in preclinical models.

To the best of the inventors' knowledge, the only similar product is a Cremophor-ethanol formulation at a strength of 10 mg/mL. In view of the undesirable properties of Cremophor, the present formulation will have substantial advantages and offer clinicians a well-tolerated product for treatment of pancreatic cancer and other solid tumors, non-malignant pancreatic disease, and, using a topical formulation, actinic keratosis or squamous cell carcinoma of the skin. Thus, clinical development of intravenous HPR further serves as proof of concept for independent neutral retinoid analogs that act independently of the RAR/RXR receptor system as chemotherapeutic agents.

The present invention is thus directed to novel formulations of HPR in the form of lipid nanoparticles for IV administration, novel HPR topical formulations, and their use in the treatment of solid tumors and cancer, particularly pancreatic cancer, and non-neoplastic pancreatic diseases, as well as dermatological precancerous and cancerous conditions. The liposomic formulations lack an added surfactant substance. In preferred embodiments, the present formulations replace the use of impure commercially-available and lecithin with defined lipids, particularly DOPC, DPPC, DMPG and DMPC (which abbreviations are set forth in full below).

The present invention provides a lipid nanoparticle composition comprising a neutral retinoid and a lipid component, wherein (a) the retinoid is dispersed in nanoparticles having diameters of less than or equal to about 1000 nm;
(b) the final concentration of the retinoid is between about 4 and about 75 mg/ml.
    (c) the lipid component is
    (i) a plant-derived lecithin acceptable for use in mammals in vivo;
    (ii) phospholipids of the lecithin of (i);
    (iii) cholic acid or a salt thereof and one or more synthetic, chemically-defined phospholipids having two fatty acid chains; or
    (iv) one or more synthetic chemically-defined phospholipids having two fatty acid chains.

The lipid nanoparticle composition preferably excludes any animal derived lecithin such as egg lecithin.

The above lipid nanoparticle preferably have diameters in the range of about 200 to about 1000 nm. In another embodiments, the particles have diameters less than or equal to about 200 nm.

The lipid nanoparticle composition preferably has a concentration of retinoid greater than or equal to 6 mg/ml, preferably between 6 and about 60 mg/ml.

In the above lipid nanoparticle composition, the retinoid is preferably HPR.

The may comprise the cholic acid or salt and the synthetic phospholipids or just the synthetic phospholipids. The phospholipids are characterized in that
(a) one or both fatty acid chains are saturated and consist of 16 or fewer carbon atoms; and/or
(b) one or both fatty acid chains are unsaturated and consist of 18 or fewer carbon atoms.

Preferably the synthetic chemically defined phospholipids comprise one or more of 1,2-dipalmitoyl-sn-3-phosphatidylcholine (DPPC), 1,2-dioleyl-sn-3-phosphatidylcholine (DOPC), 1,2-dimyristoyl-sn-3-phosphatidylcholine (DMPC) and 1,2-dimyristoyl-sn-3-phosphoglycerol (DMPG). More preferably the synthetic chemically-defined phospholipid is DMPC, DMPG or both.

In the above composition, the nanoparticles preferably have a surface charge characterized by a zeta potential of between about −50 millivolts to about +10 millivolts, more preferably between about −36 millivolts to about −11 millivolts. The zeta potential range is preferably achieved by combining two or more phospholipids having two fatty acid chains of less than or equal to 14 carbon atoms, wherein the two or more phospholipids comprise less than about 25% of the total phospholipid. The percent of the total phospholipids with glycerol head groups or the ratio of DMPC to DMPG is preferably such that the surface charge of the particles is characterized by a zeta potential of between about −50 millivolts to about +10 millivolts.

Also provided is the above lipid nanoparticle composition that is a pharmaceutical composition for intravenous or other parenteral delivery of the neutral retinoid to a human subject in need thereof, and is free of non-ionic surfactants, detergents, polyoxylated compounds, alkoxylated oils or any animal-derived substance known to be allergenic or to induce an anaphylactic reaction when administered to a human.

The pharmaceutical is preferably characterized in that, after parenteral administration to a mammalian subject, the retinoid or HPR accumulates selectively in the pancreas resulting in a pancreatic concentration that is at least four-fold higher, preferably 10-fold higher than the concentration of the retinoid or HPR in plasma. The pancreatic level is preferably at least 3.9 µg/gm (after 24 hrs).

In a preferred embodiment, the above nanoparticle composition comprises: 5 to 75 mg/ml HPR; 25 to 125 mg/ml DPPC; 10 to 75 mg/ml DOPC; 0 to 20 mg/ml DMPC; 0 to 10 mg/ml DMPG; 0.01 to 0.5 mg/ml hydroxytoluene (BHT); and 1 to 10% v/v ethanol. More preferably the above components are at concentrations of 12.5 mg/ml HPR; 64 mg/ml DPPC; 25 mg/ml DOPC; 4.14 mg/ml DMPC; 0.76 mg/ml DMPG; 0.02 mg/ml BHT; and 1-10% v/v ethanol.

Also provided is a method for producing a lipid nanoparticle formulation of a neutral retinoid, preferably HPR, comprising:
(a) dissolving the retinoid, an antioxidant and a lipid component selected from the group consisting of
    (i) a plant-derived lecithin acceptable for use in mammals in vivo;
    (ii) phospholipids of the lecithin of (i);
    (iii) cholic acid or a salt thereof and synthetic, chemically-defined phospholipids having two fatty acid chains; or
    (iv) synthetic chemically-defined phospholipids having two phospholipid chains. in a solvent or solvent mixture comprising (i) an alcohol, preferably absolute ethanol, and (ii) a chlorinated organic solvent, preferably $CH_2Cl_2$ or $CHCl_3$, or both (i) and (ii), thereby producing a solution that comprises the retinoid, the antioxidant, preferably BHT, and lipid component in the alcohol and the chlorinated organic solvent.
(b) evaporating the solvents under vacuum to produce a lipid film adhering to the vessel;
(c) reconstituting the lipid film in a non-aqueous and/or dehydrated solvent in a volume that is a fraction of an intended final volume to form a non-aqueous mixture of the retinoid and lipid;
(d) adding water in at least two steps to the solution of (c) with sonication of the solution after each step, wherein the volume of water added at each step is the same as, or greater than, the volume added in the previous step, to produce a lipid dispersion in water that comprises the retinoid;
(e) homogenizing the suspension of (d) under conditions sufficient to produce a population of lipid particles with an average diameter of less than about 1000 nm.

In step (d), the water may be added in at least five steps, or in at least 9 steps.

The lipid nanoparticles preferably have an average diameter 200 nm or less.

Preferably the lipid nanoparticles produced in step (e) are filtered through a polycarbonate filter with a pore size of about 0.2 µm to eliminate larger vesicles that are undesirable for intravenous injection into humans.

The method steps (a)-(e) may be carried out under aseptic or sterile conditions.

In addition to the retinoid, a second, lipid soluble agent to be used together with the retinoid in a pharmaceutical composition or method may be dissolved in the solvent or solvent mixture of step (a) and incorporated into the lipid film.

Also, an additional water-soluble agent, to be used together with the retinoid in a pharmaceutical composition or method, may be dissolved in the water being added in step (d).

The invention includes an emulsion composition of a neutral retinoid, preferably HPR, comprising a hydrophilic and hydrophobic phase, and comprising in combination:
(a) between about 4 and about 75 mg/ml of a neutral retinoid;
(b) a plant derived lecithin or phospholipid components from the lecithin as a hydrophobic phase present in an amount that confers upon the emulsion the following properties:
  (i) the hydrophobic phase is dispersed in the hydrophilic phase as particles having diameters in the range of about 100 nm to about 5000 nm;
  (ii) the composition is filterable through polycarbonate filters with pore sizes ranging between 0.2 µm and 5 µm without substantially altering the amount of active retinoid or the particle size range;
(c) ethanol at a concentration of between about 0.01 to about 10% v/v
(d) glycerin at a concentration of between about 5 and about 100 mg/ml, The emulsion composition is preferably a pharmaceutical emulsion composition suitable for intravenous and other parenteral administration to a human subject in need thereof, and is free of non-ionic surfactants, detergents, polyoxylated compounds, alkoxylated oils or any animal substance known to be allergenic or to induce an anaphylactic reaction when administered to a human.

The neutral retinoid or HPR is preferably present in a concentration of between about 6 and about 60 mg/ml. The particles preferably have diameters in the range of about 300 to about 3000 nm.

The invention includes a method of treating a subject having a neoplastic disease, comprising administering to the subject a therapeutically effective amount of the above pharmaceutical composition. The neoplastic disease being treated is preferably pancreatic cancer, renal cell cancer, breast cancer, and lung cancer.

The above treatment method may further comprises administering at least one additional therapeutic agent to the subject, such as least one anticancer agent.

Also included is a method of treating a subject having a disease associated with a pancreatic abnormality, comprising administering to the subject a therapeutically effective amount of the above pharmaceutical composition that accumulates preferentially in the pancreas.

Also provided is a method of delivering an agent selectively to the pancreas of a subject, comprising:
(a) incorporating the agent in a pharmaceutical composition as above to produce an agent-containing composition;
(b) administering the agent-containing composition intravenously to the subject,
wherein the agent-containing composition is delivered selectively to the pancreas In the above method the agent is preferably a therapeutic agent or a diagnostic agent.

Also provided is a topical nanoparticle composition comprising a neutral retinoid and a lipid component, wherein
(a) the final concentration of the retinoid is between about 4 and about 75 mg/ml.
(b) the lipid component is
  (i) a plant-derived lecithin acceptable for use in mammals in vivo;
  (ii) phospholipids of the lecithin of (i);
  (iii) cholic acid or a salt thereof and one or more synthetic, chemically-defined phospholipids having two fatty acid chains; or
  (iv) one or more synthetic chemically-defined phospholipids having two fatty acid chains.

Selected Abbreviations used in this document are:
ATRA—all-trans-retinoic acid
BHT—butylated hydroxytoluene
DCM—dichloromethane (=methylene chloride; $CH_2Cl_2$)
DMPC: 1,2-dimyristoyl-sn-3-phosphatidylcholine; a $C_{14}$ saturated lipid
DMPG: 1,2-dimyristoyl-sn-3-phosphatidylglycerol; a $C_{14}$ saturated lipid
DOPC: 1,2-dioleoylphosphatidylcholine $C_{18}$ saturated phospholipid
DPPC: 1,2-dipalmitoylphosphatidylcholine; $C_{16}$ saturated phospholipid
HPR(N-4-hydroxyphenylretinamide) or Fenretinide (=4HPR)
RCC—renal cell carcinoma or cancer
RES—reticuloendothelial system
SCLC small cell lung carcinoma (a neuroendocrine tumor)

DESCRIPTION OF THE PREFERRED EMBODIMENTS

Figure 1:
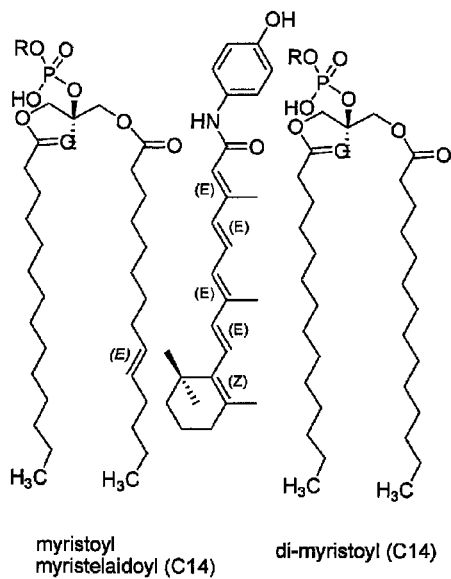
FIG. 1. Chemical structures of several defined phospholipids in physical association with HPR.
Figure 1:
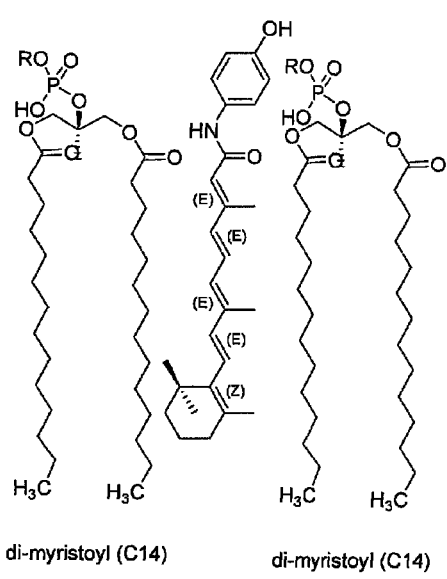
Figure 1:
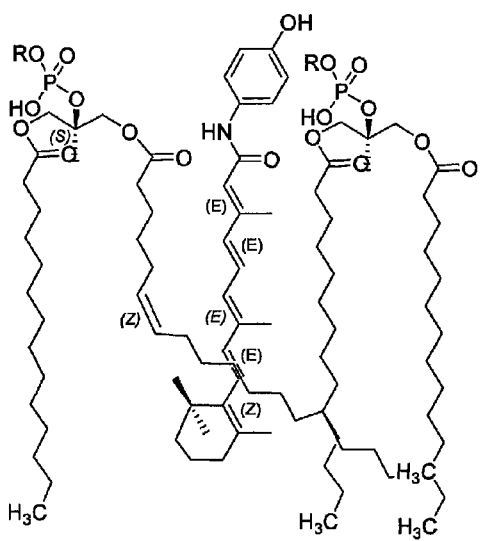
Figure 1:
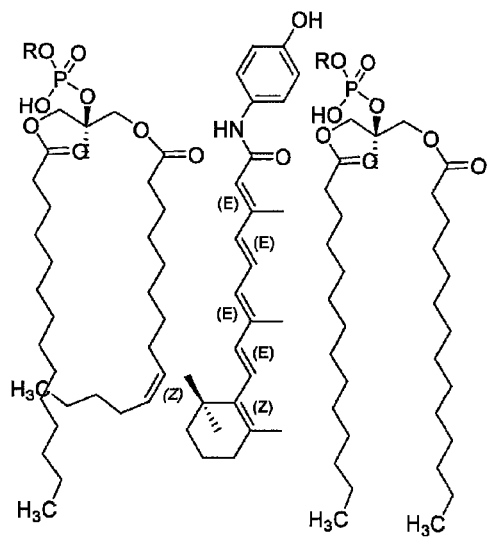

The present invention is based in part on the inventors' investigation of how chemical composition affects liposome size and stability, and has resulted in compositions of small diameter lipid nanovesicles that have preferred properties for HPR formulations and uses as described.

The formulations and method of the present invention, while focused on HPR, are intended to include any neutral retinoids—derivatives of retinoic acid. Neutral retinoids have no charged functional groups (neither acidic nor basic) at physiological pH and therefore cannot be made into salts. Compounds of this class are rather insoluble in water, having water solubility significantly below that of all-trans-retinoic acid (ATRA), 9-cis-retinoic acid or 13-cis-retinoic acid. Besides HPR, neutral retinoids within the scope of the invention include, but are not limited to the synthetic retinoid 6-[3-(1-adamantyl)-4-hydroxyphenyl]-2-naphthalene carboxylic acid (CD437) (Sun, S—Y et al., Oncogene 18:2357-65 (1999), alcohols of all-trans-retinoic acid such as such as all-trans-retinol, esters of all-trans-retinoic acid such as retinol palmitate, amides of all-trans-retinoic acid (of which HPR is an example), alcohols, esters and amides of 9-cis-retinoic acid and 13-cis-retinoic acid. Because of their known apoptotic and anti-cancer properties, HPR and CD437 are preferred.

Other retinoids, more commonly acids, have been incorporated into liposomes and some have become commercial products (e.g., Tretinoin) which have been approved for both topical and systemic administration. It is noteworthy that neutral and poorly soluble retinoids (HRP being an example of these) have not become successful clinical products. The present invention provides the necessary technology to permit such lipids to become useful drugs. Some of these may be rendered deliverable and active in vivo by substituting them for HRP according to the present invention.

During development of the various formulations, the inventors discovered a preferred lipid nanovesicle formulation of HPR designated here as "F23"). A major advantage of the present lipid nanovesicles formulations, such as F23, is that they avoid the reticuloendothelial system. Conventional and prior art liposomes are typically prepared with synthetic surfactants. In contrast, certain embodiments of the present formulations comprise, a "physiological surfactant" such as cholate that is better tolerated than Cremphor®EL or Tween and is administered in amounts less than the steady-state synthesis, or fecal excretion, of bile acids. Even better formulations of this invention, prolong the stability of preparations such as F23 by substituting synthetic defined lipids for cholate.

One objective was to remove sodium cholate as a surfactant and to add a defined lipid which might serve a similar role in conferring advantageous pharmaceutical properties on the nanoparticles. 2-dimyristoyl-sn-glycero-3-phosphocholine (DMPC) the was used. Nanoparticles generated with NF grade lecithin were found to be unstable. During their storage, the fenretinide precipitated, forming crystals. This could have been due to the change in composition from the research grade lecithin to NF grade lecithin.

To generate particles using chemically defined phospholipids (phosphatidylglycerols), molecules with several different unsaturated and saturated side chains were used, including the anionic lipid 1,2-dimyristoyl-sn-3-phospho-glycerol (DMPG) along with DMPC. To regulate the zeta potential, the phosphatidylglycerol was added.

Chemical structures of several of these lipids in combination are shown in FIG. 1. It is the present inventors' belief that the lengths and angles of the lipid chains affect the way in which HPR intercalates with these other phospholipids as parts of membranous lipid bilayers, resulting in more vs. less stable and active structures.

In embodiments employing synthetic phospholipids, DOPC/DPPC mixtures are intended to mimic the properties of lecithin. In some of the preparations tested, the sum of DMPC and DMPG concentration was held constant at 5 mg/mL to mimic the optimal concentration of cholate in other formulations, based on molarity. These compounds differ by their head groups (phosphatidyl choline vs phosphatidyl glycerol, respectively). DMPC is envisioned as plugging a "gap" between HPR and the DOPC/DPPC lipids, thereby substituting for the role played by cholate which is absent from these formulations (see FIG. 1).

The key steps required for preparing lipid nanovesicles of HPR—mixing and sonication, sterile filtration, without or without lyophilization for long-term stable storage—use processes and materials that are scalable from the laboratory to the manufacturing level, and are suitable for creating products that can be injected into human or animal patients in compliance with FDA regulations. Methods for making these nanoparticles are described in more detail in the Examples below.

The present formulations made using clinical grade HPR include solid dispersions, and three lipid-based strategies: partitioning into lipid supplements, emulsions, and lipid nanovesicles.

The lipid nanovesicle preparations yielded the highest product strength at ~50 mg/mL, superior to the strength of 2-8 mg/mL achieved with the other strategies and also far exceeding the primary solubility goal of 6 mg/mL. Thus, a preferred embodiment of the present invention is a HPR lipid nanovesicle formulation and its use in treating cancer and in selectively targeting the pancreas for treatment of either pancreatic cancer or other pancreatic diseases.

Freshly prepared lipid vesicle preparations of the present invention conform to USP specifications for IV products in terms of particle size (z) and surface charge (zeta potential). As is described in more detail below, HPR-loaded lipid nanovesicles include preparations with mean diameters of 220 nm, which are easily filterable through polycarbonate filters of pore size pertinent to sterile production (0.2 µm).

The surface or zeta potential plays an important role in the stability of colloidal systems such as liposomes and the nanoparticles of the present invention through electrostatic repulsions. Neutral and ionized phospholipids contribute to the surface charges on vesicles (Rubino, J T (1990) J Parenter Sci Technol 44, 210-15 and 247-52).

Importantly, the lipid base and surfactant of the present lipid nanovesicle formulation are physiological materials (e.g., lecithin and cholate), although, as indicated, more preferred embodiments comprise defined lipids in place of lecithin and elimination of the cholate surfactant. Such formulations are shown to be, or are expected to be, well tolerated and carry a much lower risk of allergic or hypersensitivity reactions than prior art compositions such as those comprising Cremophor®EL and similar surfactants.

The HPR lipid nanovesicle compositions of the present invention are distinct from products of the prior art in which a water-soluble drug is entrapped inside of lipid vesicles to alter the drug's release properties. Instead, the present composition comprises HPR integrated into a lipid bilayer to facilitate its action upon intravenous or topical administration. These HPR nanovesicles also differ in composition from conventional liposomes. Because of this different lipid composition of the HPR nanovesicles, they are expected to deliver HPR into tissue in a way that avoids the RES, a known problem with conventional liposomes. It is well-known that the sizes of conventional liposomes can vary depending on the method of their production. Methods for liposome preparation are described, for example, in U.S. Pat. Nos. 4,728,578, 4,728,575, 4,737,323, 4,533,254, 4,162,282, 4,310,505, and 4,921,706; International Applications PCT/US85/01161 and PCT/US89/05040; and Liposome Technology, 1984.

As exemplified below in animal studies, HPR lipid nanovesicles did not distribute preferentially into the RES, but rather, the disposition of IV injected HPR lipid nanovesicles mimicked that of oral HPR dispersed in corn oil (the only current clinical HPR product). This included preferential accumulation of HPR in the pancreas. However, there is one important difference between IV and oral administration: HPR administered IV reached higher plasma and tissue levels than when given as the oral dosage form, thereby pushing the tissue levels into the range known to be effective to achieve clinical effects, such as antitumor effects resulting from apoptosis of cancer cells.

The present invention includes use of the novel formulations as delivery vehicles for other drugs (as are conventional liposomes). However, their properties even when used in this way, represent a significant improvement over the prior art.

Without wishing to be bound to any mechanism, the present inventors discovered selective accumulation of HPR in the pancreas over other tissues of the body as a property of HPR that is not altered by significant changes to its physical form in the bloodstream.

The present embodiment of using IV HPR to treat pancreatic cancer localized in the pancreas, and other non-neoplastic pancreatic diseases, including pancreatitis and diabetes, exploits this selective accumulation property of the HPR nanovesicles.

The originally intended dose did not maintain plasma concentrations at this level but achieved plasma levels >10 µM for only a few hours each day every 3 weeks. Therefore, the lack of efficacy in Phase II clinical trials in RCC and SCLC (J Zweibel, NCI) was not surprising. To reach potentially therapeutic levels, the limitation of oral dosing on systemic exposure must be overcome or circumvented, and a key objective of the present invention is intended to develop a parenteral dosage form of HPR for solid tumor chemotherapy that maintains a minimum plasma level of 10 µM for seven days.

It is the present inventors' view that there is an underappreciated finding in the rat bioavailability study by Swanson, B N et al., (1980) *Drug Metab Dispos* 8:168-72 for commercialization of any HPR product. Not only did HPR accumulate as expected in adipose tissue and excretory organs like liver and kidney, but also quite unexpectedly, it accumulated into pancreas by a factor of 15-20 fold over plasma 24 hours after dosing. The present inventors have confirmed these findings in both mouse and rat using their preferred IV formulation.

In an early clinical trial and pharmacokinetic study of oral HPR (corn oil, soft gel capsules) administered qdx7 to adult solid tumor patients at Wayne State University, dose escalation proceeded to 1600 mg/m² TID per day for seven days (~90 capsules/day for one week). Dose escalation was halted, not because of toxicity but rather because a ceiling on HPR absorption was found that prevented plasma levels from exceeding ~5 µg/mL, regardless of schedule or dose level above 1200 mg/m² BID. The $C_{MAX}$ after the first dose was 1.0-1.3 µg/mL (2.6-3.3 µM), and climbed to 2.8-4.6 µg/mL (7-12 µM) after the last dose due to drug accumulation from a long terminal phase half-life of 8-14 hours.

Dosages of HPR Compositions for Parenteral Administration

A parenteral dosage form of HPR or other neutral retinoids is desired in order to achieve blood-plasma and tissue levels of the retinoid that are higher than can be achieved with oral administration of the currently used corn oil-based soft gel capsules. Higher blood-plasma and tissue levels than are achievable with oral dosing are desirable because recent clinical trial data showed that the oral form of HPR was only moderately effective against cancers like SCLC (B. J. Schneider et al., J Clin Oncol, 2004, 22 (14S Suppl):7299). and RCC (Vaishampayan et al., supra.

Moderate effectiveness is consistent with findings that oral dosing does not maintain blood-plasma levels above the 10 µM target concentration (3.9 µg HPR per gram of tissue (blood plasma weight is taken to be 1 g/ml) for the minimum desired 12 hours out of every day for 5-10 consecutive days, and preferably above 10 µM concentration for 72-168 consecutive hours to achieve the conditions that exhibit substantial cytotoxicity in vitro against many human tumor cell lines as reported in the literature.

In 14 patients with SCLC, the maximum concentration of HPR in blood-plasma collected 3-4 hours after the 14$^{th}$ dose of a 14 dose regimen (twice/day, morning and evening for 7 consecutive days) averaged 7.7±4.4 04 (±SD)) (Schneider et al., supra). Tumor biopsies from three RCC patients in a clinical trial at Wayne State University were analyzed for HPR content using HPLC methodology 12-22 hours after the last of 14 doses, on a treatment regimen of twice/day for 7 days (Vaishampayan et al., supra). HPR levels in tumors were 3.6, 3.8 and 7.9 µM. All these values fell below what the present inventors consider to be a 10 µM target concentration and which is preferably maintained for at least 12 hours of every consecutive day, more preferably for at least 3 days, and more preferably for the entire day for 3 and even for 7-10 consecutive days (based on in vitro studies of human tumor cell lines).

Conversion of these molar concentrations of tumor HPR to a mass basis, they correspond to 1.4, 1.5, and 3.1 µg HPR per gram of wet tissue weight. Note that a single injection of animals with a non-toxic dose of a HPR lipid nanoparticle formulation achieved tissue concentrations that persist above the target concentration of 3.9 µg per gram tissue for 24-30 hours in ⅔ PANC-1 tumor samples (growing in immunocompromised mice) and ⅔ healthy mouse pancreases, as well as in pancreas and blood-plasma of healthy rats.

By increasing the doses to tolerated levels, even if they are toxic to the extent that is commonly accepted in cancer chemotherapy practice, these HPR levels at 24-30 hours are expected to increase even more. In addition, administration of once or twice daily intravenous injections of the lipid nanoparticles, or a continuous IV infusion of several days duration, will cause the accumulation of HPR in these tissues to higher levels as well, so that they far exceed the target concentration derived from HPR effects on human tumor cell lines in vitro.

The appropriate doses of injectable HPR administered IV to achieve desired blood or tissue levels can be determined by those skilled in the art, using data from related studies of oral and intravenous HPR formulations in healthy rats. For example, the present inventors administered a single, non-toxic bolus dose of 444 mg/m² of the F23 formulation (described herein) that was prepared at a strength of 50 mg/mL HPR, via femoral vein catheters to a group of seven dual catheterized Sprague-Dawley rats. A second group of rats received a single, non-toxic dose of 1200 mg/m² HPR in corn oil via oral gavage after an overnight fast which was maintained up until 2 hours after dosing. A corn oil formulation is similar to the currently available clinical product. Blood samples were collected before treatment and at 0.25, 0.5, 1, 2, 4, 8, 24, 27 and 30 hrs after administration. The isolated plasma was tested for HPR concentrations using HPLC methodology.

Figure 2:
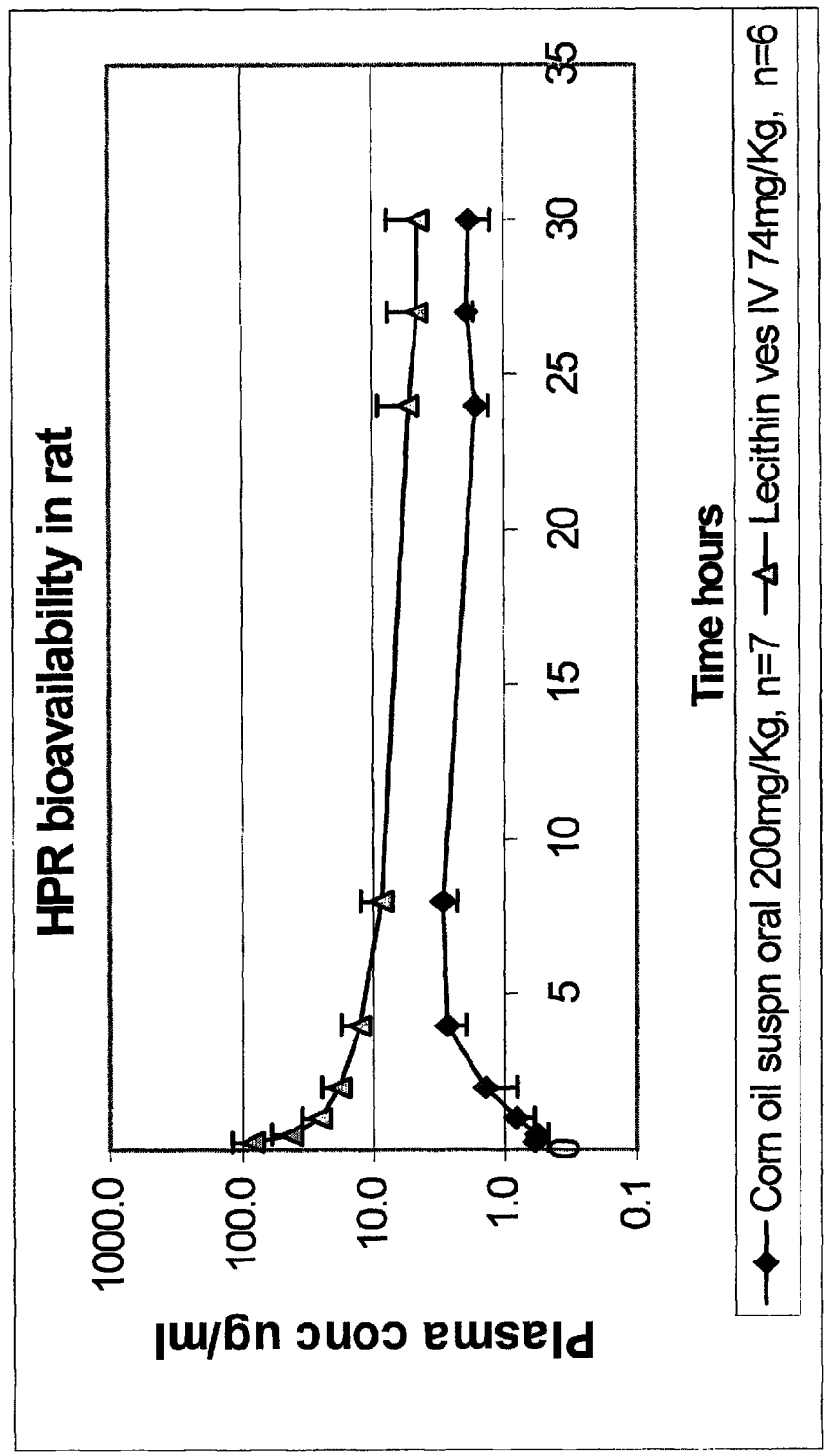
FIG. 2 is a graph of HPR bioavailability (in the rat)

Mean blood plasma concentration-time curves of measured HPR following oral and IV administration are shown in (FIG. 2). From such results, the bioavailability of the oral HPR can be calculated, as an accepted measure of the proportion of orally administered drug that entered systemic circulation. This is done by calculating the area under the curves from 0 to 30 hours ($AUC_{0-30}$) for each animal using PK software WinNonlin 3.1 and applying the trapezoidal rule. Bioavailability of oral HPR administered in corn oil was calculated by comparing the AUC values achieved by oral and intravenous dosing using the equation:

$$\% \text{ bioavailability} = \frac{AUC_{oral} \times Dose_{IV} \times 100}{AUC_{IV} \times Dose_{oral}}$$

Using this method, the bioavailability of the orally dosed HPR in the rat was calculated to be 8.0%. Assuming this to be similar to bioavailability of oral HPR in humans, which cannot be measured directly until human patients are actually dosed with intravenous HPR, it is possible to estimate suitable doses of HPR lipid nanoparticles for clinical use.

For example, in the clinical trials of oral HPR in patients diagnosed with SCLC or RCC (supra), a preferred oral HPR dose was 900 mg/m$^2$ given twice daily for 7 consecutive days every 3 weeks (3 weeks being considered 1 "cycle" of chemotherapy). Taking human bioavailability of HPR as 8%, only 8% of this oral dose will be needed with an IV formulation to achieve the same blood-plasma AUC as the oral dose. Therefore, the IV dose of HPR lipid nanoparticles required to achieve equivalent HPR exposure to that of the oral dosing in the above clinical trials is calculated to be 8% of 900 mg/m$^2$, or 72 mg/m$^2$, given twice daily for 7 consecutive days, every 3 weeks. An equivalent dose using altered schedules would be approximately 1008 mg/m$^2$ IV over a 7 day period, or 144 mg/m$^2$ per day for 7 consecutive days.

The present compositions were developed to permit parenteral administration of HPR or another neutral retinoid to achieve circulating levels for sufficient intervals that would enable the retinoid to achieve its clinical, generally therapeutic, objective, such as treating cancer in a mammalian subject, preferably a human. A primary purpose for injecting a suitable IV formulation of HPR is to achieve higher bloodplasma and tissue levels of the drug, rather merely attaining the same level of HPR as has been achieved with oral formulations. This is especially true given that the oral dose that provides the maximum amount of HPR in the human body, limited by delivery via the gut, does not cause a degree of toxicity that is acceptable in cancer therapy and is only moderately effective against these diseases. Since the above-cited study of oral dosing of HPR in SCLC patients reported a maximum plasma concentration of approximately 7.7 µM after the final of 14 doses (which translates to a cumulative dose of 12,600 mg/m$^2$, (i.e., 900 mg/m$^2$, given twice daily for 7 consecutive days), and assuming that approximately 50% of the remaining HPR in the body is eliminated every 8 hours, this blood plasma concentration will decline to just below 1 µM after 24 hours. To achieve a 24-hour concentration of HPR at or above 10 µM after an IV bolus dose, the IV dose would be increased by 10-fold to 1440 mg/m$^2$ per day.

In the clinical environment, a preferred dosing regiment would comprise continuous infusion to administer HPR IV. For example, pharmacokinetic modeling of daily IV therapy using the half-life of HPR found in the Phase I clinical trial at Wayne State University (supra) showed that a steady state will be reached after 3-4 days of daily IV therapy with an overall increase in daily concentration of ~33% (drug accumulation from the preceding doses). From such an analysis, the daily dose required to maintain HPR levels above 10 µM (~4 µg/mL) for 24 hours is estimated to be about 450 mg/m$^2$ administered daily for approximately 10 days to maintain persistent exposure to >10 µM concentration in the blood for 7 days. Based on an estimated IV dose of 450 mg/m$^2$/day to maintain plasma concentrations above 10 µM in patients, approximately 45 mL of a HPR lipid nanoparticle preparation of 20 mg/ml strength would be injected in an average sized patient.

It is noteworthy that this dose level is below the maximum tolerated dose for parenteral HPR in rodents (~650 mg/m$^2$ per day), suggesting a margin of safety when treating humans with the daily intravenous doses expected.

In general, an effective dose or amount of a formulation of the present invention is a dose that results in a sustained blood or plasma level of the active agent at a level that is statistically significantly higher than the level attained by oral dosing of any formulation of the prior art. The effective dose is effective in achieving the stated pharmaceutical/clinical objectives of the composition, including killing tumor cells, attenuating tumor growth or metastasis, accumulating in a tissue such as pancreas, or delivering an added agent associated with the composition, such as a diagnostic agent.

In one embodiment, an effective dose delivered IV is one that results in plasma HPR (or other retinoid) concentration greater than or equal to about 10 µM for the dosing period, preferably for at least about 2 days, more preferably 3 days or up to about 7 days. As is well known in the art, the circulating levels of the retinoid, is a function of both the administered dose and the frequency of administration, and it is within the skill of the art to determine without undue experimentation what dose must be administered to achieve the stated plasma levels. As discussed above, in one embodiment, the composition of the invention is injected IV once or twice per day, for a period of 7 to 10 days, followed by a rest period of up to day 21 from initiation of the treatment. This cycle is then repeated one or more times. In another embodiment, the composition is infused IV over a period of 3-6 hours in place of the one or two injections noted above. In yet another embodiment, the composition is infused continuously via an automatic pump for one to two weeks (with the pump being refilled as necessary), followed by rest for one week. This cycle is then repeated as needed. In another embodiment using continuous pump infusion, the composition is infused on alternate weeks for a period necessary to achieve the desired effect.

Those skilled in the art will know how to convert results obtained in vitro or in an animal model to a dose amount and schedule needed to treat a human subject. Thus, for example, if 5-10 µM HPR for 72 hours in vitro is generally required to achieve ≥90% killing of certain human tumor cells, then plasma concentration of 10 µM maintained for 72 hours would be expected to achieve this effect in vivo. See above. As noted above, the trial of oral HPR as a chemotherapeutic agent reached a twice daily (b.i.d.) dose of 900 mg/m$^2$ before encountering saturable absorption in all patients (without any toxicity). Dose escalation trials of the parenteral composition of the present invention would preferably begin at the dose level that will achieve equivalent systemic exposure (area under the concentration curve or "plasma AUC") to oral HPR at 900 mg/m² b.i.d.

Bioavailability of HPR in humans is determined using standard techniques a formulation of this invention administered parenterally, preferably IV. The present inventors used existing information about bioavailability of another retinoid (albeit an acid) to develop protocols for use of the present compositions. 13-cis-retinoic acid(13-cis-RA) is an organic acid which undoubtedly exhibits different intestinal absorption properties from neutral analogs like HPR Therefore, assuming ~3.5% of the 900 mg/m² oral dose is available systemically, an IV dose of 32 mg/m² given BID or a single daily IV dose of 64 mg/m² would be a suitable starting dose of the present HPR composition. At the upper end of a normal body surface area (2 m²), the calculation yields an IV dose of 128 mg/day. Delivered in a 100 ml infusion would require a solution HPR concentration of only 1.3 mg/mL However, the IV product would preferably be packaged in a 10-20 ml vial that would be diluted in USP Saline or distilled water (D5W) for infusion. A 20 ml vial at 6 mg/mL dispensed into the 100 ml would achieve a daily dose of ~120 mg.

Thus, a preferred starting dose for an HPR IV product would be set at 6 mg/mL, i.e., a potency that would support the starting dose in a Phase 1 clinical trial. It would appear that pushing plasma HPR levels to the range known to induce apoptosis in human tumor lines will require a 10-20 fold increase in daily dose above the starting dose of (640-1280 mg/m²), which means achieving a combination of product "volume x concentration" that delivers daily IV doses of 1200-2400 mg HPR, (e.g., 20-40 ml vials of HPR at 60 mg/mL. However, pharmacokinetic modeling of daily IV therapy using the terminal phase half-life of HPR found in the Phase I clinical trial revealed to the inventors that steady state would be reached after 3-4 days of daily IV therapy with an overall increase in daily concentration of ~33% due to drug accumulation. From such analysis, the daily dose required to maintain HPR levels >10 µM (~4 µg/mL) for the entire 24 hour period is ~450 mg/m², which must be administered for a minimum of 10 days to reach the minimum therapeutic target of exposure of >10 µM for 7 days. It is important to note that this dose level is below the maximum tolerated dose ("MTD") of 651 mg/m² in rodents, suggesting a broad margin of safety for humans treated with a daily dose that is expected to cause solid tumor regression.

Thus, the present invention achieves a formulation vial strength of ~60 mg/mL via optimization of the HPR product, because 20 ml vialed product of HPR at this concentration would support dose escalation above expected pharmacologically-active dose levels. As shown, 50 mg/mL vial strength was achieved using the lipid nanovesicles of this invention.

The parenteral pharmaceutical compositions of the present invention can be administered by any appropriate route for the disease or condition being treated. The administration may be intravenous, the preferred route, subcutaneous, topical, intramuscular, intradermal, intraarterial, intraperitoneal, intralesional including intratumoral, intrathecal, intracranial, intraarticular, intravesical, intraprostatic, intrapericardial, intrapleural, intratracheal, intranasal, intravitreal, vaginal, rectal, mucosal, and the like. Administration may be local, regional, or systemic. Administration may be by aerosol (lung instillation), injection, infusion, continuous infusion, localized perfusion bathing target cells directly or via a catheter and/or lavage. As disclosed herein the present composition are formulated for parenteral administration with concern primarily for IV injection or infusion. The preparation of such pharmaceutical compositions beyond the specific formulations disclosed herein are known to those of skill in the art (See for example, Gennaro, A E., *Remington: The Science and Practice of Pharmacy*, Lippincott Williams & Wilkins Publishers; 2003 or latest edition); *Pharmaceutical Analysis*, Watson D, ed. (1999 or later edition), Harcourt Pub Ltd, London). For human administration, it will be understood that the preparations meet the sterility, pyrogenicity, general safety and purity standards required by FDA Office of Biological Standards and other relevant regulatory bodies.

Treatment of Various Diseases and Conditions with HRP Compositions

The compositions of the present invention are intended as pharmaceutical compositions for the treatment of any disease that is treatable by the administration of a neutral retinoid, most preferably HPR. The HPR formulations described herein, produced by methods disclosed herein, are used as a potent anticancer agent alone or in combination with other anti-cancer agents or therapeutic modalities.

As noted above and exemplified herein, HPR is useful for killing tumor or cancer cells, and is expected to act similarly on any hyperproliferative cell.

Thus, the present methods are directed to the treatment of any of a number of cancers, including solid tumors and leukemias and lymphomas.

Malignant and metastatic diseases and conditions (tumors and cancer) which can be treated in accordance with the present invention include, but are not limited to, solid tumors, e.g., carcinomas, sarcomas, lymphomas and other malignant or nonmalignant tumors such as those listed below. For a review of such disorders, see any textbook of clinical oncology, e.g., *Cancer: Principles & Practice of Oncology*, 5th Ed. (DeVita, V. et al., eds), Philadelphia: Lippincott-Raven Publishers, 1997 or later edition).

Nonlimiting examples of cancers that are treated by the present compositions are pancreatic carcinomas, renal cell carcinomas, small cell lung carcinoma, non-small cell lung carcinoma, prostatic carcinoma, bladder carcinoma, colorectal carcinomas, breast, ovarian, endometrial and cervical cancers, gastric adenocarcinoma, primary hepatocellular carcinoma, genitourinary adenocarcinoma, thyroid adenoma and adenocarcinoma, melanoma, retinoblastoma, neuroblastoma, mycosis fungoides, pancreatic carcinoma, prostatic carcinoma, bladder carcinoma, myeloma, diffuse histiocytic and other lymphomas, Wilms' tumor, Hodgkin's disease, adrenal tumors (adrenocortical or adrenomedullary), osteogenic sarcoma, soft tissue sarcoma, Ewing's sarcoma, rhabdomyosarcoma and acute or chronic leukemias, islet cell cancer, cervical, testicular, adrenocortical, or adrenomedullary cancers, choriocarcinoma, embryonal rhabdomyosarcoma, Kaposi's sarcoma. A further list of cancers treatable by the present invention (including some of the above) is:

acoustic neuroma
Adenocarcinoma
angiosarcoma
astrocytoma
basal cell carcinoma
bile duct carcinoma
bladder carcinoma
breast cancer
bronchogenic carcinoma
cervical cancer
chondrosarcoma
choriocarcinoma
colorectal carcinomas
craniopharyngioma cystadenocarcinoma
embryonal carcinoma
endotheliosarcoma
ependymoma
esophageal carcinoma
Ewing's tumor
fibrosarcoma
gastric carcinoma
Glioma/glioblastoma
Head and neck cancers
Hemangioblastoma
Hepatocellular carcinoma
Hepatoma
Kaposi's sarcoma
leiomyosarcoma
liposarcoma
lung carcinoma
lymphangiosarcoma
lymphangioendotheliosarcoma
Lymphoma
Leukemia
medullary carcinoma
medulloblastoma
Melanoma
meningioma
mesothelioma
Multiple myeloma
Myxosarcoma
Nasopharyngeal carcinoma
Neuroblastoma
oligodendroglioma
osteogenic sarcoma
ovarian cancer
pancreatic cancer
papillary adenocarcinomas
pinealoma
prostate cancer
renal cell carcinoma
retinoblastoma
rhabdomyosarcoma
sebaceous gland carcinoma
seminoma
small cell lung carcinoma
squamous cell carcinoma
sweat gland carcinoma
synovioma
testicular tumor
Thyroid cancer
Wilms' tumor Premalignant and non-neoplastic (=non-malignant) diseases that are considered to be "hyperproliferative disorders" and that are treated by the present compositions and methods include, but are not limited to, myelodysplastic disorders; cervical carcinoma-in situ; familial intestinal polyposes such as Gardner syndrome; oral leukoplakias; histiocytoses; keloids; hemangiomas; hyperproliferative arterial stenosis, inflammatory arthritis; hyperkeratoses and papulosquamous eruptions, virus-induced hyperproliferative diseases such as warts and Epstein-Barr Virus EBV induced disease (e.g., infectious mononucleosis), scar formation, etc. The present methods of treatment may be used on any subject known or suspected of having or being at risk of developing a hyperproliferative disorder.

Treatment of cancer, a tumor, a premalignant disease or a hyperproliferative disorder by the present compositions includes the killing, inhibiting or slowing the growth of the relevant target cells, or inhibiting the increase in size of a tumor or cancerous growth. This includes, reducing cell numbers, or preventing metastasis. "Treatment" as used herein is not meant to imply total cure or disappearance of cancer of a growing tumor. "Treatment" or "treating" is also intended to include prophylaxis, i.e., the prevention of development of a tumor or cancer, either primary, metastatic or recurrent.

The topical compositions of the present invention are particularly useful to treat cancerous, pre-cancerous and inflammatory skin conditions responsive to HPR alone or in combination with other suitable drugs. These conditions include but are not limited to actinic or solar keratosis, melanoma, and non-melanoma skin cancers such as basal and squamous cell carcinomas, as well as psoriatic disease.

The present compositions can be formulated in aerosols for lung instillation for treating lung cancer. Other lung diseases that benefit from alveolar delivery of HPR or other neutral retinoids are also contemplated.

The selective accumulation of HPR in the pancreas after IV administration is exploited herein to treat pancreatic cancer localized in the pancreas. The present compositions are administered IV to treat non-neoplastic diseases of both the exocrine and endocrine pancreas, including diabetes (Type I and Type II), pancreatitis, pancreatic insufficiency, or enzyme deficiencies in the pancreas (for example, by delivery, in or associated with the nanovesicles, gene therapy vectors encoding the deficient enzymes.

Selective accumulation in other tissues, such as liver and kidneys, may similarly be exploited to treat diseases of those organs.

It should be evident that for selective delivery of the HPR formulations to the pancreas (and elsewhere) in the treatment of non-neoplastic diseases, noncytotoxic formulations of HPR are preferred.

Storage and Stability of HPR Lipid Nanovesicles

During storage of an injectable formulation such as HPR lipid nanoparticles, it is important to monitor not only the stability of the chemical content (such as the HPR concentration) but also the stability of the lipid particle size and other physical properties such as zeta potential, using a special instrument like a Zetasizer 3000 (see Examples) to analyze vesicle size and Zeta potential. This is more important when antioxidants, for example BHT, are used in the formulations, because BHT can stabilize the chemical integrity of HPR against degradation by oxidation without affording any protection to the physical integrity of the lipid nanoparticles themselves. Thus, measurements of physical properties of the lipid particle preparations, in particular zeta potential and particle size, are recommended for establishing the stability of these formulations under storage conditions.

Using the F23 formulation prepared from research grade lecithin supplemented with cholate, the freshly prepared lipid nanosystem formulation initially exhibited charge and size characteristics within USP specifications for injectable products intended for IV administration, and were therefore suitable for studies of IV injections into animals.

For example, preparations using the F23 formulation containing 20 or 50 mg/ml HPR were found to contain lipid nanoparticles of mean diameters 250 or 210 nm, respectively, which are well below the present inventors' goal for particles with mean diameters <1 µm and the USP requirement of mean diameters <5 µm for intravenous products. These preparations were filterable through an Isopore membrane of pore size 0.4 µM after 2 weeks of refrigerated storage (and after 1 week of ambient storage) in the dark, and were found to contain at least 95% of the original amount of soluble HPR.

The polycarbonate filters used are scalable to the manufacturing scale, and can be used with stainless steel, high-pressure filter holders that can be autoclaved for producing sterile product.

One important physical property of the nanoparticles is zeta potential, which did not change over one month in storage. However, vesicle size (diameter) of two preparations increased during 1-month storage from <1 µm to approximately 8-16 μm, exceeding USP specifications noted above, rendering this product unsuitable for IV injection into humans.

Based on these findings, some embodiments of the present HPR lipid nanoparticle formulations are preferably prepared fresh for use, including possibly being made fresh on each day of use. Other lipid nanoparticle formulations that use different sources of lecithin, and especially formulations that are made from synthetic phospholipids, exhibit stable physical properties in storage for 6 months or longer, including HPR content, zeta potential and particle diameter.

HPR Lipid Nanoparticles as Carriers of Other Agents

The nanoparticles of the present invention may be used as carriers to bring other drugs, diagnostic molecules, or other agents to wherever these particles accumulate, such as to the pancreas where they accumulate selectively. If the drug to be carried is lipid-soluble, then it is incorporated during Step (1) of the production process, above, when dissolving the HPR and "structural lipids" of the nanoparticles. It is possible to view the BHT preservative, incorporated into the present nanoparticles, as such a "payload," and this has been done successfully.

The "other" agents may be diagnostic agents as well as therapeutic agents. Preferred additional therapeutic agents are anticancer agent, such as chemotherapeutic drugs, radiotherapeutic agents, a immunotherapeutic agents, a gene therapy agents, a hormone therapy agents, other biological agents, as well as an additional retinoid or a retinoid derivative. Chemotherapeutic agents and methods of their administration, dosages, etc. are well known to those of skill in the art. See for example, Gennaro A R, ed., supra (or latest edition); *Pharmaceutical Analysis*, Watson, D., ed. First Ed 1999: Harcourt Pub Limited London, UK; *Goodman & Gilman's The Pharmacological Basis of Therapeutics*, Brunton, L L et al., eds, 11th edition, McGraw-Hill Professional, New York, 2005; *Physicians Desk Reference*—latest edition), Drugs or other agents that are water-soluble may be incorporated as payload into the HPR nanoparticles of the present invention during the reconstitution/hydration step as described. They are simply dissolved at the desired concentration in the water being used to hydrate the lipids. Agents that are active in the pancreas and treat diseases involving that organ are particularly preferred (for example, inhibitory RNA (RNAi) molecules to block the inflammatory processes of pancreatitis). Drugs that act on the endocrine pancreas and affecting islet cell activity, viability, etc. in the treatment of diabetes are also included.

Although this is not considered traditional "targeted delivery" that generally refers to the presence of specific ligands to deliver drugs or liposomes, etc., the selective accumulation of HPR into certain tissues may be considered "concentrated delivery," although its mechanism is still obscure. When delivering other substances via the HPR nanovesicles, emulsions and other formulations of the present invention, it is important that the presence of the additional substance(s) not compromise the ability of these nanoparticles to accumulate selectively in the indicated tissues.

The present invention includes "combination therapy" in which the present pharmaceutical compositions comprising a retinoid, preferably HPR, are administered in conjunction with other conventional, or even yet-to-be discovered, anti-cancer agents or treatment approaches. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing tumor size, inhibiting a tumor growth, inhibiting tumor-stimulated angiogenesis or otherwise reducing the blood supply to a tumor, promoting an anti-tumor immune response, preventing or inhibiting the progression of a cancer, or increasing the lifespan of a subject with a cancer. Anti-cancer agents include chemotherapeutic and, radiotherapeutic agents, surgical procedures, immunotherapeutic agents, gene therapy agents, and the like. In general such an agent is provided in combination with a pharmaceutical composition of the present invention in ways and amounts effective to kill or block proliferation of a cancer cell. This may involve providing both the HPR composition and the other agent to cancer cells at the same time, or sequentially.

The terms "contacted" and "exposed," When applied to a cell, tissue or organism, the term "contacting" or "exposing" are used interchangeably to describe delivery to a target cell, tissue or organism. To achieve cytotoxicity or inhibition of growth, the present composition and/or additional agent(s) are delivered to one or more cells in a combined amount effective to kill the cell(s) or prevent their continued growth.

Delivery of Diagnostic Agents by HRP Formulations

The HPR nanovesicles of the present invention may be "diagnostically labeled" meaning that they are associated with a diagnostically detectable label that can be delivered selectively to a tissue, such as the pancreas, by the mechanism discussed above. Many different labels exist in the art and methods of labeling are well known the skilled artisan. General classes of labels, which can be used in the present invention, include but are not limited to, radioactive isotopes, paramagnetic isotopes, compounds which can be imaged by positron emission tomography (PET), fluorescent or colored compounds, compounds which can be imaged by magnetic resonance, chemiluminescent compounds, bioluminescent compounds, etc. Suitable detectable labels include, but are not limited to, radioactive, fluorescent, fluorogenic or chromogenic labels. Useful radiolabels (radionuclides), which are detected simply by γ counter, scintillation counter or autoradiography include, but are not limited to, $^3$H, $^{125}$I, $^{131}$I, $^{35}$S and $^{14}$C.

Methods and compositions for complexing metals to proteins or peptides are well known in the art. The peptide protein can be one that is formulated with the HPR in the nanovesicles or other formulations of the invention. The metals are preferably detectable metal atoms, including radionuclides, and are complexed to proteins and other molecules (See, e.g., U.S. Pat. Nos. 5,627,286, 5,618,513, 5,567,408, 5,443,816 and 5,561,220).

Common fluorescent labels include, but are not limited to, fluorescein, rhodamine, dansyl, phycoerythrin, phycocyanin, allophycocyanin, o-phthaldehyde and fluorescamine (Haugland, *Handbook of Fluorescent Probes and Research Chemicals*, Sixth Ed., Molecular Probes, Eugene, Oreg., 1996) may be used to label compounds of structural formula (I). Fluorescein, fluorescein derivatives and fluorescein-like molecules such as Oregon Green™ and its derivatives, Rhodamine Green™ and Rhodol Green™, are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green™ derivatives with substituents on the nitrogens are preferred labeling reagents. This group includes the tetramethylrhodamines, X-rhodamines and Texas Red™ derivatives. Other preferred fluorophores are those excited by ultraviolet light. Examples include, but are not limited to, cascade blue, coumarin derivatives, naphthalenes (of which dansyl chloride is a member), pyrenes and pyridyloxazole derivatives.

Inorganic materials such as semiconductor nanocrystals (Bruchez, et al., 1998, Science 281:2013-2016) and quantum dots, e.g., zinc-sulfide-capped Cd selenide (Chan, et al., Science 1998, 281:2016-2018) may also be used as diagnostic labels.

The nanoparticles can also be labeled with fluorescence-emitting metals such as $^{152}Eu$ or others of the lanthanide series. These metals can be attached through acyl chelating groups such as diethylenetriaminepentaacetic acid (DTPA), ethylene-diamine-tetraacetic acid (EDTA), etc.

Radionuclides may be included in, or attached to, the nanoparticles either directly or indirectly using an acyl chelating group such as DTPA and EDTA for in vivo diagnosis. The chemistry of chelation is well known in the art and varying ranges of chelating agent to peptide may be used to provide the labeled peptide. Of course, the labeled peptide must retain the biological activity of the native peptide.

Any radionuclide having diagnostic or therapeutic value can be used as the radiolabel in the present invention. In a preferred embodiment, the radionuclide is a γ-emitting or beta-emitting radionuclide, for example, one selected from the lanthanide or actinide series of the elements. Positron-emitting radionuclides, e.g. $^{68}Ga$ or $^{64}Cu$, may also be used. Suitable γ-emitting radionuclides include those which are useful in diagnostic imaging applications. The γ-emitting radionuclides preferably have a half-life of from 1 hour to 40 days, preferably from 12 hours to 3 days. Examples of suitable γ-emitting radionuclides include $^{67}Ga$, $^{111}In$, $^{99m}Tc$, $^{169}Yb$ and $^{186}Re$.

Examples of preferred radionuclides (ordered by atomic number) are $^{67}Cu$, $^{67}Ga$, $^{68}Ga$, $^{72}As$, $^{89}Zr$, $^{90}Y$, $^{97}Ru$, $^{99}Tc$, $^{111}In$, $^{123}I$, $^{125}I$, $^{131}I$, $^{169}Yb$, $^{186}Re$, and $^{201}Tl$.

A number of metals (not radioisotopes) useful for magnetic resonance imaging include gadolinium, manganese, copper, iron, gold and europium. Gadolinium is most preferred, in the form of complexed Gd-DTPA. Generally, the amount of the present composition needed for detectability in diagnostic use will vary depending on considerations such as age, condition, sex, and extent of disease in the patient, contraindications, if any, and other variables, and is to be adjusted by the individual physician or diagnostician.

General Description of Topical Formulations

Method for making preferred topical formulations and their composition are described in the Examples below. See, for example, Gennaro A R, supra for disclosure of topical pharmaceutical carriers, excipients, etc., A "topical carrier" or a "topically acceptable vehicle" refers to a carrier, a diluent, or a dispersant capable of delivering the formulated HPR nanoparticles to an appropriate layer of the skin without undue toxicity, irritation, allergenicity or the like. The topical formulations described in the Examples incorporate the necessary vehicle into the formulation, or may be formulated further to improve their delivery. A topical carrier may also possesses favorable cosmetic properties. Most preferred topical carriers are organic materials in which the nanoparticles can be dispersed. Sagarin, E et al., 1972, *Cosmetics, Science and Technology*, 2d ed., 1:48-65), incorporated herein by reference, contains numerous examples of suitable topically acceptable topical carriers. Examples include various emollients, emulsifiers, humectants, thickeners and powders, and solvents (including water) as described below.

The topically acceptable vehicle will usually form from 5% to 99.9%, preferably from 25% to 80% by weight of the active composition, and can (in the absence of other adjuncts) form the balance of the composition.

The topical formulations of the invention may also contain additives and adjuvants which are conventional in the pharmaceutical, dermatological or cosmetic arts, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the art, and, for example, range from 0.01% to 10% of the total weight of the composition. Depending on their nature, these additives and adjuvants may be introduced into the fatty phase, into the aqueous phase.

Hydrophilic gelling agents include carboxyvinyl polymers (carbomer), acrylic copolymers such as acrylate-alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

Among polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Another category of functional ingredients that may be used in the topical compositions of this invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol®. Gums may be employed such as xanthan, carrageenan, gelatin, karaya, pectin, and locust beans gum. Under certain circumstances the thickening function may be accomplished by a material also serving as a silicone or emollient. For instance, silicone gums in excess of 10 centistokes and esters such as glycerol stearate have dual functionality.

Having now generally described the invention, the same will be more readily understood through reference to the following examples which are provided by way of illustration, and are not intended to be limiting of the present invention, unless specified.

The EXAMPLES below describe formulations of non-allergenic, highly-soluble preparations of HPR, prepared in several forms using several methods, none of which involve surfactants or other ingredients that would necessitate co-medication of humans or animals who received these formulations.

Example 1

Type 1. Free-Flowing Lipid Nanosystem

Type 1. Free-flowing lipid nanosystems were prepared by hand using research grade soy lecithin (in particular a formulation designated F23 that was the lead formulation demonstrating in vivo efficacy against human tumors). Such free-flowing lipid nanosystems of HPR substantially increased the water solubility of HPR to as high as 50-60 mg/ml, more than 1000-× its natural water solubility. These free flowing nanosystems can be prepared generally using the following approach.

HPR, research grade soy lecithin (or other source of phosphatidyl lipid), BHT (or other appropriate antioxidant to protect the HPR from oxidation), and cholic acid (or another appropriate additive that physically stabilizes the lecithin nanodispersion and facilitates particle formation, are dissolved in a 1:1 mixture of methanol:chloroform and the solvents removed under vacuum, preferably in a rotating evaporation flask so that the materials are deposited as a thin film onto the wall of the round flask. After adding some ethanol to re-wet the film (an amount of ethanol that will yield its final concentration of 5-10% by volume after addition of the water in the next step) and vortexing, water is added up to the final volume, and the preparation mixed. The resulting lipid vesicles are size reduced to a size suitable for intravenous injection by sonication for approx 20 min in a water bath sonicator to obtain a free flowing nanosystem product that can solubilize HPR to these high levels as judged by the ability of the formulation to transfer at least 80% of the HPR content of the product through polycarbonate membranes with sub-micron pore sizes (pore size ratings <1 μm).

A typical preparation was made by mixing the following ingredients per ml of formulation: 50 mg HPR, 165 mg of soy lecithin (as a 40% solution), 45 mg cholic acid, 0.1 ml absolute ethanol, 0.02 mg BHT, and the reminder of the 1 ml volume achieved with water suitable for parenteral use in humans.

Additional preparations of free-flowing lipid nanosystems of HPR can be achieved in formulations representing a range of content for individual ingredients. Tables 2-4 show individual formulations that yielded free-flowing nanosystems containing chemically stable HPR, the composition of which resulted in a range of HPR concentrations and concentrations of other ingredients such as soy phosphatidyl choline or sodium cholate:

TABLE 2

| | Formulation | | | | | | |
|---|---|---|---|---|---|---|---|
| Ingredient | F1 | F2 | F3 | F7 | F9 | F11 | F13 |
| Fenretinide (mg) | 20 | 20 | 20 | 50 | 50 | 20 | 50 |
| Soy Lecithin (phosphatidyl-choline) (mg) | 45 | 110 | 165 | 110 | 165 | 45 | 165 |
| Sodium cholate (mg) | 15 | 36 | 54 | 36 | 54 | 15 | 55 |
| BHT (mg) | | | | | | 0.02 | 0.02 |
| Ethanol (ml) | 0.1 | 0.1 | 0.1 | 0.1 | 0.1 | 0.1 | 0.1 |
| Distilled water (ml) D5W (ml) | 0.9 | 0.9 | 0.9 | 0.9 | 0.9 | 0.9 | 0.9 |

Formulations F1-F3 (20 mg/mL HPR) were prepared initially and were found to be free flowing, and the HPR chemically stable. Formulations F7 and F9 provide formulations that can be used to achieve an aqueous solubility of HPR of 50 mg/ml, using either 36-54 mg/ml cholate. Formulations 11 and 13 represent preparations similar to F1 and F3, respectively, except that the antioxidant BHT has been added. HPR is susceptible to oxidative damage, and clinically useful products with acceptable storage stability are anticipated to contain antioxidant(s). Levels of BHT used were within the limits of acceptable human daily doses assuming that as much as 2000 mg of HPR from these preparations would be administered with each dose twice per day to human patients. Inclusion of BHT did not in any way affect the formulation properties or stability of the preparations, and so BHT was included as an antioxidant as standard practice in all additional formulations. The particle sizes of F11 and F13 were determined using a Zetasizer 3000 (at Malvern Instruments) and were confirmed to fall within USP limits for intravenous administration when freshly prepared. HPR content was quantified using an HPLC method against a standard curve of HPR from the US National Cancer Institute.

Cholesterol is generally known as a stabilizer of phospholipid membranes, and a general method of preparing liposomes is to dry an organic solvent solution of lecithin plus cholesterol and then reconstitution in an aqueous solution followed by sonication to spontaneously form liposomes, However, it was not possible to solubilize HPR in free-flowing lipid nanosystems after adding cholesterol to the preparations, because phase separation was observed in the preparations containing cholesterol within one week of preparation and the nanosystem could not be readily re-dispersed after phase separation had occurred. Thus, standard ingredients for preparing conventional free-flowing lipid nanosystems of cholesterol-containing lipid membranes were not successful with HPR preparations. Examples of cholesterol-containing liposome formulations that failed in our studies are provided in Table 3

TABLE 3

| | Formulation | | | | |
|---|---|---|---|---|---|
| Ingredient | F4 | F5 | F6 | F8 | F10 |
| Fenretinide (mg) | 20 | 20 | 20 | 50 | 50 |
| Soy Phosphatidylcholine (Lecithin) (mg) | 55 | 110 | 165 | 110 | 165 |
| Sodium cholate (mg) | 18 | 36 | 54 | 36 | 54 |
| Cholesterol (mg) | 27.5 | 55 | 82.5 | 55 | 82.5 |
| BHT (mg) | | | | | |
| Ethanol (ml) | 0.1 | 0.1 | 0.1 | 0.1 | 0.1 |
| Distilled water (ml) D5W (ml) | 0.9 | 0.9 | 0.9 | 0.9 | 0.9 |

Instead, the free-flowing lipid nanosystems containing HPR were more stable when membrane stabilizers other than cholesterol were used, for example, sodium cholate, polyoxylated surfactants such as Tween 80, or chemically-defined, shorter chain di-myristoyl-phosphatidyl-glycerol or di-myristoyl-phosphatidyl choline lipids. HPR formulations containing sodium cholate at 15-55 mg/ml yielded free-flowing nanoparticles. However, a single intravenous administration of such a formulation (e.g., F15) to mice, which contains a non-toxic dose of HPR of 300 mg/m2 (50% of the published maximum tolerated dose of HPR in rats, when administered intraperitoneally in DMSO solvent), caused a brief stupor in all injected animals accompanied by increased heart rate, from which they recovered after 2-3 minutes. This was suspected to be an effect of sodium cholate on cardiovascular function, because cholate reportedly possesses digitalis-like activity. However, several formulations of free-flowing lipid nanodispersions of 12.5 mg/ml HPR could be prepared (formulations F16 to F19). The F16 formulation did not yield a homogenous preparation, illustrating that 2.5 mg sodium cholate is not high enough to produce free flowing lipid nanosystems that solubilize HPR. However, in contrast, F17, F18 and F19 were homogeneous preparations, illustrating that sodium cholate contents ranging from 5-10 mg/ml are sufficient to achieve high aqueous solubility of HPR, but the resulting lipid vesicles were larger in size than F11 and F13 and probably too large for IV administration, as they could not be filtered through 0.22 μm filter. Combining the lowest sodium cholate content (5 mg/ml) from the acceptable range represented by F17-F19 (5-10 mg/ml) with a reduced level of soy phosphatidylcholine (25 mg/ml, instead of 45-165 mg/ml) resulted in free-flowing lipid nanoparticles only when ethanol was included to a level of 0.10 or 0.05 ml per ml (i.e., 10% or 5% v/v) —represented by formulations F20 and F23. Formulations prepared without ethanol were not homogenous and drug deposits (insoluble drug) were observed on the walls of the container, whether prepared in a water-base (F21) or in a 5% dextrose-water base (F22). Results with F21 and F22 illustrate that ethanol at a concentration of 5-10% of the volume of the formulation was required to achieve free-flowing lipid nanovesicle systems. F20 and F23 could be sterile filtered with a 0.22 μm filter. F23 appeared homogeneous and was selected over F20 for in vivo studies in animals because of lower alcohol content.

TABLE 4

| Ingredient | Formula | | | | | | | | |
|---|---|---|---|---|---|---|---|---|---|
| | F15 | F16 | F17 | F18 | F19 | F20 | F21 | F22 | F23 |
| Fenretinide (mg) | 12.5 | 12.5 | 12.5 | 12.5 | 12.5 | 12.5 | 12.5 | 12.5 | 12.5 |
| Soy Phosphatidylcholine (Lecithin) (mg) | 45 | 45 | 45 | 45 | 45 | 25 | 25 | 25 | 25 |
| Sodium cholate (mg) | 15 | 2.5 | 5 | 7.5 | 10 | 5 | 5 | 5 | 5 |
| Cholesterol (mg) | | | | | | | | | |
| Tween 80 (mg) | | | | | | | | | |
| BHT (mg) | 0.02 | 0.02 | 0.02 | 0.02 | 0.02 | 0.02 | 0.02 | 0.02 | 0.02 |
| Ethanol (ml) | 0.1 | 0.1 | 0.1 | 0.1 | 0.1 | 0.1 | — | — | 0.05 |
| Distilled water (ml) | 0.9 | 0.9 | 0.9 | 0.9 | 0.9 | 0.9 | 1 | — | 0.95 |
| D5W (ml) | | | | | | — | — | 1 | — |

The cholate content of a preparation made using this component should be safe to administer IV. F23 originated in optimization studies to reduce cholate levels below acutely toxic amounts in mice without losing essential pharmaceutical characteristics of the lipid preparation. IV injections into the mouse confirmed that F23 did not cause acute toxicity in contrast to earlier lipid vesicle preparations. Calculations of the amount of soybean lipid that will be infused with this preparation indicate that the levels will be well tolerated without toxicity. Based on an estimated IV dose of 450 mg/m$^2$/day to maintain target plasma levels (>10 μM) in patients, ~16 mL of this preparation are infused over a period of 4 hours into a 70 kg patient, so the rate of lipid infusion is <6 mg/Kg/hour, which is far below the levels reported to be toxic for soybean oil based emulsions (Klein, S et al., (1994) *JPEN J Parenter Enteral Nutr* 18:396-97).

Example 2

Type 2 Free flowing Lipid Nanosystem Based on Lecithin

Type 2 free flowing lipid nanosystems were prepared using scalable pharmaceutical manufacturing techniques and processes, especially lecithin-based preparations from an ethanol+dichloromethane (DCM;=methylene chloride or CH$_2$Cl$_2$) solvent.

Similar preparations of highly soluble HPR in soy lecithin can also be prepared after solubilizing the lipid ingredients in different solvents than methanol plus chloroform. For example, a preparation of water soluble HPR at ~11.4 mg/ml was produced from a lipid film made from drying a 1:1 solvent mixture of ethanol: DCM. To prepare this, 5400 mg L-α-phosphatidylcholine and 300 mg sodium cholate were added to a rotary evaporation round bottom flask, to which was then added 60 ml of a 1:1 mixture of DCM:ethanol, and sonicated until the materials dissolved. Then, 300 μl of a 4 mg/mL solution of BHT in ethanol was added to the flask and dissolved by hand swirling. Next, 750 mg of HPR was added to the flask and dissolved into the mixture using sonication. The flask was attached to a Buchi rotary evaporator in a 40° C. water bath, with its receiving flask in a wet ice bath and a secondary vacuum flask packed in dry ice placed between the instrument and the vacuum source. The rotary evaporator was operated at a setting of 45-46 rpm and the vacuum pump operated at a setting of 24 in. Hg for 6.8 hrs while chilled water was circulated through the condenser of the rotary evaporator. At the end of the evaporation period, the rotary evaporator was stopped, the vacuum was released to ambient conditions, and ~51 ml of solvent were recovered from the receiving flask of the instrument plus the in-line vacuum flask.

The evaporation flask containing the dried lipid HPR film was stored in the dark at 2-8° C. Two days later, the lipid film was reconstituted by adding 3.0 ml dehydrated alcohol (USP injection grade) and sonicating in a water bath for ~20 minutes, while maintaining the water temperature between ambient indoor room temperature and 35-37° C. by periodical addition of tap water. ~63 ml of water were added to the flask in a stepwise manner in nine graded addition steps with increasing volumes. The preparation was sonicated for 1 minute after each step. The volume of water added in each of the nine steps was: 0.33 ml, 0.33 ml, 0.84 ml, 1.5 ml, 3.0 ml, 4.5 ml, 9.0 ml, 13.5 ml, and 30 ml, resulting in total of 63 mL of water.

This resulted in a viscous, free-flowing lipid system, yellow in color that contained sub-μm to μm-sized vesicles when observed microscopically. ~30 ml of this preparation was further processed in an Avestin C-5 homogenizer instrument. The hydrated product was homogenized at 10,000 psi for a total of 3 passes through the homogenizer, using compressed N$_2$ gas to drive the homogenization. Upon completion of homogenization, the product was collected and the pressure in the homogenizer instrument was reduced to 0 psi. The instrument was then used to pass the homogenized product through an extruder equipped with a polycarbonate, track-etched screen filter membrane (GTTP type) rated at 0.2 μm pore size. The homogenization step yielded a transparent yellow solution which easily passed through the GTTP type filtration membrane of the extruder without creating any measurable back-pressure and after which vesicles could no longer be detected using a microscope. After storage in the dark for two days at either room temperature or 4° C., the preparation remained transparent yellow solutions with no evidence of precipitants or larger lipid vesicles. This preparation was observed again after 18 days and ~3 months of storage and was found to remain a transparent yellow solution without any detectable vesicles or crystals (by phase contrast microscopy; 40× objective and 10× eyepieces).

Homogenizing the same preparation for six passes (vs. the 3 passes used successfully as described above) created a product that appeared unstable ~3 months of storage in the dark at ambient temperatures but that was stable after the same period at 4° C. These findings suggest that over-homogenization may damage the product.

Example 3

Type 3—Free Flowing Lipid Nanosystems of Phosphatidyl Lipids

Type 3—free flowing lipid nanosystems were prepared using scalable pharmaceutical manufacturing techniques and processes that contained shorter-chain phosphatidyl lipids as a substitute for the cholic acid/cholate salt ingredient.

Natural soy lecithin (natural L-α-phosphatidylcholine") contains predominantly $C_{16}$ and $C_{18}$ fatty acid side chains covalently attached to the C-1 and C-2 carbons of the glycerol backbone of the lecithin molecule. The $C_{16}$ fatty acids are commonly saturated. The $C_{18}$ fatty acids are commonly unsaturated, with one or more double bonds in the carbon atom backbone.

The HPR formulations prepared using natural soy lecithins from various sources would be expected to show similar compositions. It is possible to use chemically-defined phosphatidyl choline lipids with shorter chain fatty acids than $C_{16}$ or $C_{18}$ on the C-1 and C-2 positions of the glycerol backbone as a substitute/replacement for cholic acid (or cholate salt) to prepare free-flowing lipid nanosystems that achieve high water solubility of HPR, preferentially those with carbon backbones smaller than 16 atoms with an even numbers of carbon atoms (as examples, $C_{14}$, $C_{12}$, or $C_6$ fatty acids). A synthetic phosphatidyl choline with a saturated fatty acid with a carbon backbone of 14 carbon atoms acylated to both the C-1 and C-2 positions of the glycerol backbone can be used (1,2-dimyristoyl-sn-glycero-3-phosphocholine).

For example, a preparation of water soluble HPR at ~12.5 mg/ml was produced from a lipid film made from drying a 1:1 solvent mixture of ethanol and dichloromethane. To prepare this, 2700 mg L-α-phosphatidylcholine and 237 mg 1,2-dimyristoyl-sn-glycero3phosphocholine were added to a rotary evaporation round bottom flask, to which was then added 30 ml of a 1:1 mixture of DCM:ethanol, and sonicated in a water bath until the materials dissolved in the solvent, while maintaining the water temperature in the water bath between ambient indoor room temperature and 35-37° C. by periodically adding tap water. Then, 150 µl of a 4 mg/mL solution of BHT in ethanol was added to the flask and dissolved by swirling. Next, 375 mg of HPR was added to the flask and dissolved into the mixture using sonication. The flask was attached to a Buchi rotary evaporator in a 40° C. water bath, with its receiving flask in a wet ice bath and a secondary vacuum flask packed in dry ice placed between the instrument and the vacuum source. The rotary evaporator was operated at a setting of 45-46 rpm and the vacuum pump operated at a setting of ~25 in. Hg for 10.5 hrs, while chilled water was circulated through the condenser of the rotary evaporator. At the end of the evaporation period, the rotary evaporator was stopped, the vacuum was released to ambient conditions, and the evaporation flask containing the dried lipid film of HPR was stored overnight in the dark at 2-8° C. The next day, the lipid film was reconstituted in the flask by adding 1.5 ml dehydrated alcohol (USP injection grade) and sonicating in a water bath until the film was reconstituted into the liquid, while maintaining the temperature in the water bath between ambient indoor room temperature and 35-37° C. by periodic addition of tap water. ~28.5 ml of water were added to the flask in a stepwise manner in nine graded addition steps with increasing volumes. The preparation was again sonicated for ~1 minute between each step, and then for an additional 10 minutes after the last portion of water. The volume of water added in each of the steps was: 0.165 ml, 0.165 ml, 0.42 ml, 0.75 ml, 1.5 ml, 2.5 ml, 6 ml, 7 ml, and 10 ml, resulting in total addition of ~28.5 mL water. This resulted in a yellow, viscous, free-flowing lipid system.

The preparation was removed from the flask and further processed in an Avestin C-5 homogenizer instrument. The hydrated product was homogenized at 15,000 psi for a total of 4 passes through the homogenizer, using compressed $N_2$ gas to drive the homogenization. Upon completion, the product was collected and the pressure in the homogenizer instrument was reduced to 0 psi. The instrument was then used to pass the homogenized product through an extruder equipped with a polycarbonate, track-etched screen filter membrane (GTTP type) rated at 0.2 µm pore size. The homogenization step yielded a translucent, nearly transparent, yellow solution, which easily passed through the GTTP type filtration membrane of the extruder without creating any measurable back-pressure, after which vesicles could no longer be detected using a microscope.

After membrane extrusion, the collected preparation was characterized using a Zetasizer Nano® instrument (Malvern Instruments) and found to contain nanoparticles with an average Z-value of ~338 nm and a zeta potential of approximately −31.5 mV. After dilution by 4-fold or 40-fold, the formulation contained nanoparticles with average Z-values that varied with the type of diluent and also with the extent of dilution, but in all cases, the particle sizes ranged from approximately 58 to 100 nm and the zeta potential from approximately −11 to −51.5 mV. These are acceptable ranges for intravenous administration. The preparation was stable after storage in the dark for approximately 1 or 7 days at 4° C., and remained a translucent, nearly transparent, yellow solution with no evidence of precipitation of formation of larger lipid vesicles. After approximately 23 days, this preparation was found to contain a small number of larger vesicles but no crystals or other signs of HPR precipitation (by phase contrast microscopy; 40× objective and 10× eyepieces).

Example 4

Type 4—Free Flowing Lipid Nanosystem of Phosphatidyl Lipids

Type 4—free flowing lipid nanosystems made with lecithins of USP grade, NF grade or drug master file (DMF) grade and using shorter-chain phosphatidyl lipids in place of cholic acid/cholate, using scalable pharmaceutical manufacturing techniques and processes
Lipid Nanosystem Type 4A Not all natural soy lecithins (natural L-α-phosphatidylcholines) possess the consistent quality and purity required for use in commercial products intended for human and veterinary use. Soybean lecithin can be a complex mixture of phospholipids, including those other than phosphatidyl cholines, plus smaller quantities of glycolipids, triglycerides, sterols, free fatty acids, carbohydrates and/or sphingolipids. Commercial products benefit from soy lecithin materials that contain consistent compositions to achieve consistent manufacturing and product performance.

Free flowing lipid nanosystems of highly water-soluble HPR have been prepared using soy lecithin of a grade suitable for human and/or veterinary use, while at the same time substituting 1,2-dimyristoyl-sn-glycero-3-phosphocholine for cholic acid/cholate and using scalable pharmaceutical manufacturing techniques and processes to prepare the formulations.

In this example, a preparation of water-soluble HPR at ~12.5 mg/ml was produced using a soy lecithin product named Phospholipon 90G® from American Lecithin. This product, manufactured under cGMP, is certified to contain ≥94% phosphatidylcholine with no other phospholipid impurities and is supported by Drug Master Files at regulatory agencies in the USA and Canada. It is intended for the manufacture of liposomes or emulsions that are to be used, for example, for parenteral administration.

237 mg 1,2-dimyristoyl-sn-glycero-3-phosphocholine (DMPC) was added to a rotary evaporation round bottom flask to which were added 10 ml of ethanol to solubilize the DMPC using a swirling motion. Then, 2700 mg of Phospholipon 90G was added to the flask, followed by 15 ml of chloroform. Next, 0.15 ml of a 4 mg/ml solution of BHT in ethanol was added, followed by the addition of 375 mg HPR. The ingredients were mixed and dissolved by manual swirling. The flask in a 40° C. water bath was attached to a Buchi rotary evaporator, with its receiving flask in a wet ice bath and a secondary vacuum flask packed in dry ice placed between the instrument and the vacuum source. The rotary evaporator was operated at a setting of 150-200 rpm and the vacuum pump operated at a setting of ~25 in. Hg for 10.5 hrs, while chilled water was circulated through the condenser of the rotary evaporator. After overnight evaporation, the rotary evaporator was stopped, the vacuum was released back to ambient conditions, and the evaporation flask containing the dried lipid film of HPR was removed. The lipid film was reconstituted in the flask by first adding 1.5 ml dehydrated alcohol (USP injection grade) and sonicating in a water bath for ~60 minutes with intermittent manual swirling, while maintaining the water temperature in the water bath between ambient indoor room temperature and 35-37° C. by periodically adding tap water.

Approximately 28.5 ml of water were added to the flask in a stepwise manner in nine graded addition steps with increasing volumes. The preparation was again sonicated for ~1 minute between each step, and then for an additional 10 minutes after the last portion of water. The volume of water added in each of the steps was: 0.165 ml, 0.165 ml, 0.42 ml, 0.75 ml, 1.5 ml, 2.5 ml, 6 ml, 7 ml, and 10 ml, resulting in total addition of ~28.5 mL water. This resulted in a yellow, viscous, free-flowing lipid system.

The preparation was removed from the flask and further processed in an Avestin C-5 homogenizer instrument. The hydrated product was homogenized at 15,000 psi for a total of 5 passes through the homogenizer, using compressed $N_2$ gas to drive the homogenization. Upon completion, the product was collected and the pressure in the homogenizer instrument was reduced to 0 psi. The instrument was then used to pass the homogenized product through an extruder equipped with a polycarbonate, track-etched screen filter membrane (GTTP type) rated at 0.2 µm pore size. The homogenization step yielded a yellow non-transparent solution, which easily passed through the GTTP type filtration membrane of the extruder without creating any measurable back-pressure. After membrane extrusion, the preparation was separated into separate containers for storage in the dark at ambient room temperature and at 4° C.

The next day, the stored preparation was characterized using a Zetasizer Nano® instrument (Malvern Instruments) and found to contain nanoparticles with an average Z-value of ~177 nanometers and a zeta potential of approximately –4.6 mV. After 40-fold dilution with 10 mM NaCl or a clinically suitable 5% dextrose solution ("D5W USP") and overnight storage at 4° C., the preparation contained nanoparticles with average Z-values of approximately 110 nm or 116 nm, respectively, and with zeta potentials of approximately –7.0 mV or –5.6 mV, respectively.

Similarly, when the preparation was stored overnight at ambient room temperature and diluted by 40-fold with 10 mM NaCl or D5W, it was found to contain nanoparticles with average Z-values of approximately 120 nm or 117 nm, respectively, and zeta potentials of approximately –4.4 mV or –3.6 mV, respectively.

After storage in the dark at ambient room temperature or at 4° C., an analysis revealed that the size and surface electrostatic charge of the nanoparticles was stable under both conditions, with ranges shown in Table 5 below.

TABLE 5

| Storage period | Size Average Z value | Surface Charge Zeta potential |
| --- | --- | --- |
| 1 week | 104-121 nm | –2.8 to –5.7 mV |
| 1 month | 104-112 nm | –5.3 to +5.0 mV |
| 3 months | 103-122 nm | –6.3 to 8.7 mV |

Lipid Nanosystem Type 4B

This system is similar to Type 4A above lipid nanovesicles, above, with some differences in the process steps. In this example, as above, a water-soluble HPR preparation (~12.5 mg/ml) was produced using Phospholipon 90G® as above. This product was also manufactured under cGMP and is certified to contain ≥94% phosphatidylcholine with no other phospholipid impurities.

Phospholipon 90G, 2700 mg, was added to a rotary evaporation round-bottom flask that already contained 10 ml ethanol and was dissolved by manual swirling. Then, 150 mg of cholic acid (Na salt) was added and dissolved by sonication. Next, 375 mg of HPR was added to the flask, followed by 15 ml of chloroform and then 0.15 ml of a 4 mg/ml solution of BHT in ethanol. These ingredients were mixed and dissolved by manual swirling of the flask and the same process steps as described in Example A were carried out.

The dried lipid film of HPR was reconstituted in the flask by first adding 1.5 ml dehydrated alcohol (USP injection grade) and sonicating as above. As above, ~28.5 ml of water were added to the flask in a stepwise manner in nine graded addition steps with increasing volumes using the same steps as described above. After the same homogenization steps, the process resulted in a yellow, translucent product.

The product was characterized as above and was found to contain nanoparticles with Z-average value of ~361 nm and zeta potential of approximately –24 mV. After a 40-fold dilution into either 10 mM NaCl or D5W USP, analysis revealed nanoparticles with a Z-average value of ~69 nm or ~78 nm, respectively, and a zeta potential of approximately –18 mV or –26 mV, respectively.

The product was divided into separate containers for storage in the dark at ambient room temperature (RT) or 4° C. for four intervals (overnight, 1 week, 1 month and 3 months). No detectable microscopic changes were observed during storage under either condition. As shown in Table 6, after storage at 4° C. for the indicated time periods, the preparation contained nanoparticles with stable Z-average values when diluted 40-fold into 10 mM NaCl and slightly more variable values when diluted 40-fold into D5W USP. The nanoparticles exhibited stable Zeta potentials when diluted into 10 mM sodium chloride, again, with more variability when diluted into D5W USP. The results were generally similar for samples stored at RT. Again, Z-average values were stable when the preparation was diluted into 10 mM NaCl sodium chloride and somewhat more variable when diluted into D5W USP. At these storage temperatures, Zeta potentials were also stable when diluted into 10 mM NaCl, whereas more variability was observed when the particles were diluted into D5W USP

TABLE 6

| Duration of storage at temp | | Avg. Z value in nm Particles diluted into: | | Zeta potential in mV Particles diluted into: | |
|---|---|---|---|---|---|
| | | 10 mM NaCl | D5W USP | 10 mM NaCl | D5W USP |
| Overnight | 4° C. | 70 | 81 | −19 | −29 |
| 1 week | 4° C. | 69 | 78 | −18 | −29 |
| 1 month | 4° C. | 69 | 201 | −19 | −8.7 |
| 3 months | 4° C. | 64 | 73 | −16 | +8.3 |
| Overnight | RT | 69 | 80 | −20 | −28 |
| 1 week | RT | 69 | 78 | −22 | −26 |
| 1 month | RT | 85 | 116 | −20 | +3.1 |
| 3 months | RT | 88 | 90 | −17 | +10.9 |

Lipid Nanosystem Type 4C

For this formulation, 2700 mg of Lecithin, Granular, NF was added to a rotary evaporation round bottom flask containing 5 ml of ethanol. The subsequent steps were as described in the previous Examples for this type of formulation. 237 mg DMPC were added to the flask followed by BHT and ethanol as above. This was followed by the addition of 375 mg of HPR. These ingredients were mixed, dissolved and vacuum dried as in Type 4A above. The HPR-containing lipid film was reconstituted as above and the nine step process of adding water in aliquots of increasing volumes was employed.

This resulted in a yellow, viscous, free-flowing lipid system which was homogenized as in the previous example. The homogenization step yielded a yellow, non-translucent material containing no vesicles large enough to be detected by phase microscopy performed as above.

The preparation was characterized for vesicle size and surface charge as above and was found to contain nanoparticles with Z-average value of ~147 nm and a zeta potential of approximately −29 mV. After 40x dilution in 10 mM NaCl, the average Z value of the nanoparticles was approximately 95 nm and the zeta potential was approximately −62 mV. Similar dilution into D5W USP yielded an average Z value of approximately 118 nm and zeta potential of approximately −39 mV. The product was divided into separate containers for storage in the dark at ambient room temperature (RT) or 2-8° C. for six intervals (overnight, 1 week, 10 days, 1 month and 3 months and 6 months). No detectable microscopic changes were observed during storage under either condition. As shown in the Table below, The preparation was divided into separate containers for storage in the dark for 1 week, 10 days, 1 month, 3 months and 6 months at ambient room temperature or at 2-8° C. After brief (10 day) storage at 2-8° C., the average Z values and zeta potential were as shown in Table 7 below.

TABLE 7

| Avg. Z value in nm Particles diluted into: | | Zeta potential in mV Particles diluted into: | |
|---|---|---|---|
| 10 Mm NaCl | D5W USP | 10 mM NaCl | D5W USP |
| 90 | 132 | −63 | −38 |

After storage in the dark at 2-8° C. for approximately 3 months, the product was stable based on light and phase contrast microscopy. Stable HPR content measured by HPLC ranged from 84-109% of the expected concentration of 12.5 mg/ml. However, this preparation was not stable after storage of more than about 3 months in the dark at either ambient room temperature or at 2-8° C.

Example 5

Type 5—Free Flowing Lipid Nanosystems of HPR Made with Synthetic Phospholipids

In this example, free flowing lipid nanosystems of HPR were made from synthetic phospholipids with or without surfactants such as cholic acid/cholate using scalable pharmaceutical manufacturing techniques and processes.

Instead of using lecithin from natural plant sources like soybeans and soy products, HPR formulations of nanoparticles were prepared using entirely synthetic chemicals. Formulations of various compositions with similarly useful pharmaceutical and pharmacological properties, can be produced by varying the amounts of synthetic versions of phosphatidylcholine, phosphatidylglycerol, phosphatidic acid, and other phospholipids to substitute for the lecithin and lecithin-based materials in the formulations such as those above made using natural, non-animal sources like soy.

According to the present invention, similar to the use of natural lecithin and phosphatidylcholine, synthetic phospholipids may be combined with cholic acid/cholates to produce free-flowing lipid nanosystems of highly water soluble HPR. These preparations offer the advantage of greater purity of composition and greater consistency between individual preparations because the synthetic ingredients can be better controlled than natural materials prepared from plant sources, making them preferably for preparation of parenteral pharmaceutical formulations for use in humans and/or animals as therapeutics or delivery vehicles.

In contrast to natural soy lecithin that contains amounts of $C_{16}$ and $C_{18}$ saturated and unsaturated fatty acids acylated to the C-1 and C-2 positions of the glycerol backbone that vary from batch to batch, synthetic phospholipids contain chemically defined content of the acylated fatty acids in the phospholipids that provides for very making consistent formulated products to and very consistent compositions.

In this example, a preparation of water soluble HPR at ~12.5 mg/ml was produced from entirely synthetic phospholipids using the following procedure.

22.8 mg of 1,2-dimyristoyl-sn-glycero-3-[phospho-rac-(1-glycerol)] (sodium salt) ("DMPG"), 124.2 mg of 1,2-dimyristoyl-sn-glycero-3-phosphocholine ("DMPC"), and 750 mg of 1,2-dioleoyl-sn-glycero-3-phosphocholine ("DOPC") were added to a rotary evaporation round bottom flask containing 15 ml of chloroform. The flask was subjected to the same steps described above.

Next, 1920 mg of 1,2-dipalmitoyl-sn-glycero-3-phosphocholine (DPPC) were added, sonicated for 5 minutes to dissolve the DPPC, while maintaining the water bath temperature.

Then, 14.85 ml of 375 mg of HPR in ethanol was added to the flask, followed by the addition of BHT in ethanol as above, and subsequent sonication and incubation as above.

Rotary evaporation was conducted as above, but for 44.5 hours. The dried lipid film of HPR was reconstituted in the flask by adding 1.5 ml dehydrated alcohol (USP injection grade) and sonicating in a water bath for approximately 4 hours until the film was reconstituted into the liquid. ~28.5 ml of water were added to the flask in nine graded additions as above. This resulted in a yellow, viscous, free-flowing lipid system.

The preparation was removed from the flask homogenized as above, yielding a non-translucent, yellow solution which was filtered as above. After this, vesicles were undetectable (microscopically). After membrane extrusion as above and overnight storage at ambient room temperature in the dark, the collected preparation was characterized as described above and found to contain nanoparticles with a Z-average value of ~400 nm and a zeta potential of approximately –10 mV.

After a 40-fold dilution into either 10 mM NaCl or D5W USP, analysis revealed nanoparticles with a Z-average value of ~115 nm or ~132 nm, respectively, and zeta potentials of approximately –9.2 mV and –20 mV, respectively.

The product was divided into separate containers for storage in the dark at ambient room temperature (RT) or 2-8° C. for four intervals (overnight, 1 week, 1 month and 3 months). When analyzed after 40-fold dilution into 10 mM NaCl, the product was found to be stable in storage in the dark at either set of temperatures. See Table 8.

TABLE 8

Ranges in Particle size and Charge after Storage overnight, 1 week, 1 month, and 3 months

| Storage Temperature | Range of Avg. Z value in nm Particles diluted into: | | Range of Zeta potential in mV Particles diluted into: | |
|---|---|---|---|---|
| | 10 mM NaCl | D5W USP | 10 mM NaCl | D5W USP |
| 2-8° C. | 105-108 | 120-135 | –10 to –12 | –20 to +2.8 |
| Room Temp. | 111-115 | 127-172 | –8.6 to –12 | –19 to +3.1 |

It is noted that Z-average and zeta potential values varied more widely during storage when analysis was conducted after 40-fold dilution into D5W.

After storage in the dark at either 2-8° C. or ambient room temperature for approximately 6 months, the product was stable as judged by visual and phase microscopic observation and by HPLC measurement of HPR levels (which ranged from ~83-97% of the expected concentration of 12.5 mg/ml).

Increasing the DMPG content resulted in a more negative zeta potential (see table). The DMPG wt % is the weight % of the DMPG content of the total phospholipid content (per ml). A log-linear relationship was found between zeta potential and % DMPG. Reducing DMPG content to 0.89% did not further lower the zeta potential. Instead the particles had zeta potential of –11 mV similar to particles generated with 1.43% DMPG content. Preparations lacking DMPG resulted in neutral zeta potential. The size distribution was not related to the DMPG content.

| DMPG wt % | Mean particle size (Z) in (nm) | Zeta Potential (mV) |
|---|---|---|
| 0.89 | 119 | –11 |
| 1.43 | 85 | –11.4 |
| 1.91 | 88 | –14.5 |
| 2.79 | 50 | –20.2 |
| 4.1 | 101 | –25.0 |
| 5.7 | 64 | –28.9 |
| 9.5 | 67 | –36.1 |
| 15 | 69 | –42.1 |

After storage of the nanoparticles with zeta potentials ranging from 0 to –42 mV, it was observed that the particles with DMPG content of 1.43% or less were physically stable. The nanoparticles remained dispersed without aggregation or crystallization. Based on these results, it was decided to select the formulation with a DMPG content of 0.89% to maintain zeta potential away from neutrality but within the range of existing products with FDA marketing approval. The preferred formulation has been physically and chemically stable in dark at 4° C. and ambient storage conditions for over 6 months, and its compliance with USP requirements for IV products indicates suitability as a pharmaceutical product for delivering HPR intravenously at doses as high as 3,000 mg per day (1800 mg/m$^2$/d).

Studies in mice and rats at an IV dose of 450 mg/m$^2$ have shown the product to be well tolerated without any signs or symptoms of toxicity. In the absence of any serious toxicities, achieving this dose level via IV administration would represent a 20-fold increase in the systemic availability of HPR over that achieved with the oral dosage form. Oral gel caps shown partial success in that they caused stable disease in Phase II trials by the present inventors and their colleagues for SCLC (Schneider, B J et al., supra) and RCC (Vaishampayan et al., supra) despite poor bioavailability. It is therefore expected that by surpassing the systemic exposure level achieved by the oral product, the IV formulation of the present invention will result in tumor regression or a wider clinical efficacy profile.

Example 6

The Ratio of Synthetic Chemically-Defined Phospholipids Permits Precise Titration of Zeta Potential and Control of Storage Stability The lipid nanoparticles in this Example were made Entirely from Synthetic Materials, with or without surfactants like cholic acid/cholate, using scalable pharmaceutical manufacturing techniques and processes.

Phosphatidyl cholines with shorter acyl side chains than naturally occurring $C_{16}$ and $C_{18}$ fatty acids in soy and other plant-derived sources can replace the requirement for cholic acid/cholate salt or surfactants in lecithin-based formulations of HPR nanoparticles. An example of such a phosphatidyl choline is 1,2-dimyristoyl-sn-glycero-3-phosphocholine ("DMPC").

Type 3 and 4 formulations, discussed above, can also be incorporated into formulations of HPR nanoparticles that are produced entirely from synthetic chemicals. In addition to the number of C atoms in the acylated fatty acids bonded to the C-1 and C-2 position of the glycerol backbone, the phospho head group of phospholipids can be bonded to a variety of polar head groups such as choline, glycerol, ethanolamine (or have nothing bonded, is the case with phosphatidic acid).

These polar head groups confer different charge properties on the part of the phospholipids that extend from the surface of lipid membranes into the surrounding water phase. Hence, polar head groups of varying composition in HPR free-flowing lipid nanoparticle formulations can be used for more precise control of particle charge density and therefore control important pharmaceutical properties like zeta potential and storage stability.

This is illustrated by the properties of a series of free-flowing lipid nanoparticle formulations containing a number of molecules (moles) of phospholipids composed only of C-14 saturated acyl side chains ("di-myristoyl" fatty acid chains) that equals the concentration (moles/ml) of cholate used in the soy lecithin-based formulations of HPR.

A series of formulations are created by altering the proportion of $C_{14}$ phospholipids that have choline or glycerol polar head groups. As expected, the HPR nanoparticles in these formulations differ in their zeta potentials and also in their long-term stabilities upon storage (in the dark at 2-8° C. and at ambient RT).

This example shows a mathematical relationship between the proportion of the $C_{14}$ phospholipids containing glycerol versus choline head groups and the zeta potential of the nanoparticles, that allows prediction of desired zeta potentials of nanoparticles produced in accordance with this invention.

By extrapolation to other combinations of shorter chain phospholipids with differing polar head groups, it is now possible to substitute these lipids for surfactants while at the same time precisely controlling the zeta potential and stability of nanoparticle formulations.

A series of preparations of water soluble HPR (~12.5 mg/ml) was produced from entirely synthetic phospholipids. Varying amounts of two $C_{1-4}$ acyl side chain phospholipids known as DMPG (sodium salt)) and DMPC were added to a rotary evaporation round bottom flasks using the methods described above.

The amount of each lipid added to a flask was carefully selected so that the total amount of the two lipids combined was consistently 4.9-5.0 mg/ml. The mount of one lipid was increased as the amount of the second lipid decreased. Next, 750 mg DOPC was added to each flask. The flasks were sonicated and incubated as described above.

Next, 1920 mg of DPPC was added to each flask, which was sonicated and incubated as above. Then, 14.85 cc of ethanol containing 375 mg of HPR was added to each flask, followed by the addition of BHT in ethanol as above. The flasks, processed one at a time, were subject to evaporation as above for 44.5 hrs.

The dried lipid film of HPR was reconstituted in the flask as above adding 28.5 cc of water using the 9-step procedure. The preparation was again sonicated for ~1 minute between each step of water addition, and then for an additional 10 minutes after adding the last portion of water. This resulted in a yellow, viscous, free-flowing lipid system. The preparation was removed from the flask subjected to homogenization and filtration/extrusion as above, yielding a moderately translucent, yellow solution in which vesicles were undetectable by phase microscopy.

The Z-average particle diameter and zeta potential of the collected preparations were characterized as above (see Table 9).

Then, the preparations were divided into separate containers for storage in the dark for six different intervals (overnight, 1 week, 1 month, 3 months, 6 months and 12 months) at either RT or at 2-8° C. At the end of each storage period, the preparations were re-analyzed for size, electric charge, and chemical determination of the HPR content.

Table 9 shows the impact of the proportion of DMPG and DMPC in free flowing lipid HPR nanoparticle preparations on zeta potential. Also shown is the effect on stability of storage for 6 months (at ambient room RT temperature in the dark).

These results show that stable HPR nanoparticles (≥6 months; RT) characterized by a zeta potential in the range of −11 to −4.6 mVolts could be obtained by selecting appropriate DMPG and DMPC concentrations.

TABLE 9

| Phospholipon 90G | DPPC mg/ml | DOPC mg/ml | DMPG mg/ml | DMPC mg/ml | Zeta (mV) | Size (nm) | 6 month stability at RT |
|---|---|---|---|---|---|---|---|
| 90 | 0 | 0 | 0 | 7.9 | −4.6 | 120 | Yes |
| 0 | 64 | 25 | 0.76 | 4.14 | −11 | 119 | Yes |
| 0 | 64 | 25 | 1.2 | 3.7 | −11 | 76 | Yes |
| 0 | 64 | 25 | 1.7 | 3.3 | −16 | 88 | No |
| 0 | 64 | 25 | 2.4 | 2.5 | −20 | 50 | No |
| 0 | 64 | 25 | 3.6 | 1.4 | −24 | 101 | No |
| 0 | 64 | 25 | 5 | 0 | −29 | 64 | No |

1. All formulation were prepared with 12.5 mg/ml HPR and 0.02 mg/ml BHT.

Product made with DMPG levels >1.2 mg/ml was unstable upon storage at RT (in the dark)

Figure 3:
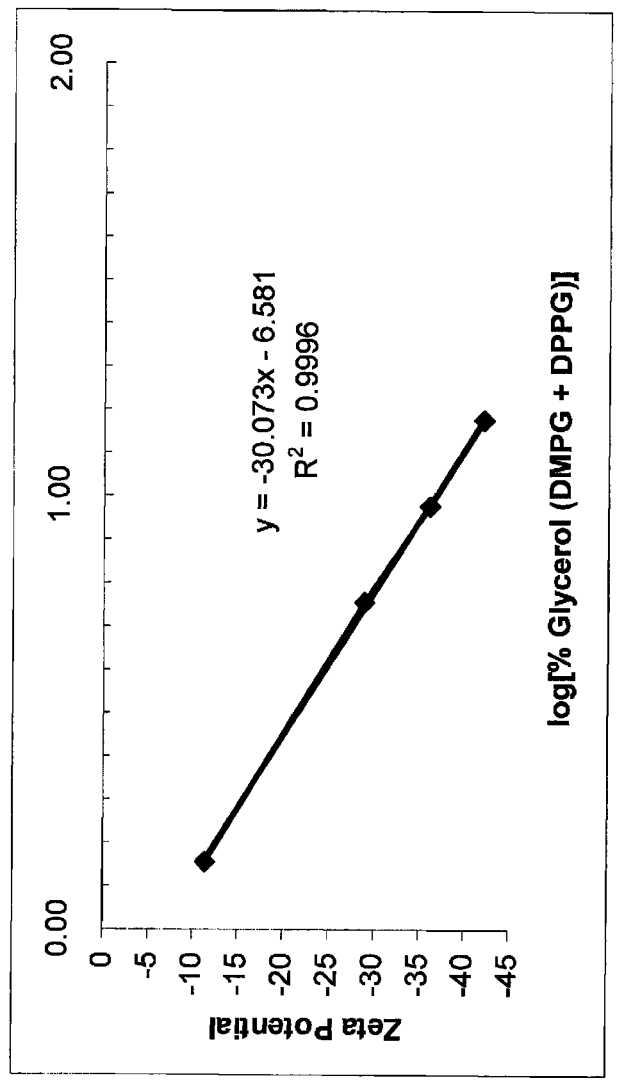
FIG. 3 is graph showing a mathematical relationship between the % Composition of glycerol polar head groups per ml of formulation and the Zeta Potential of the resulting HPR nanoparticles in a series of formulations of defined content of chemically synthetic phospholipids. The glycerol polar head groups in the formulations were the sum of the masses of DMPG and DPPG, and the percent glycerol is the mass represented by these glycerol head group lipids as a percent of the total mass of the phospholipids in the formulation.

FIG. 3 illustrates the mathematical relationship between the content of glycerol polar head groups (per ml of formulation) and the Zeta Potential of the resulting HPR nanoparticles in a series of formulations of defined content of synthetic phospholipids. The glycerol polar head groups in the formulations were the sum of the masses of DMPG and DPPG. The percent glycerol is the mass represented by these glycerol head group lipids as a percent of the total mass of the phospholipids in the formulation.

The mathematical relationship can be used to predict the zeta potential of any desired HPR preparation comprising synthetic phospholipids DPPC plus DOPC. Similar mathematical relationships can be derived from other pairs of $C_{14}$ (or shorter chain) phospholipids, and knowledge of such relationships is used to control the pharmaceutical properties and storage stabilities of such other synthetic free-flowing phospholipid nanosystems.

Example 7

Production of Cytotoxic and Non-Cytotoxic Free Flowing Lipid Nanosystems for Various Medical Applications Free flowing lipid nanosystems of HPR based on plant-derived phospholipids substantially increase the water solubility of HPR so that much higher doses of HPR can be administered to human or animal subjects than can be achieved by oral dosing of existing gel capsules of the corn oil suspension. Because the current oral dosage form of HPR has shown clinical effectiveness in the treatment of human renal cell cancer and human small cell lung cancer, the higher doses achieved by parenteral administration of the novel formulations of the present invention will achieve greater chemotherapeutic effectiveness. Administration of the lipid nanosystems described herein will not require pre-medication to prevent allergic reactions, because the compositions are made without surfactants or animal products like egg-derived lecithins that cause human allergies.

As discussed in the Background section, HPR has attracted interest as a cancer chemotherapeutic because of its apoptotic action, seen most dramatically on human small cell lung carcinoma cells in vitro. This effect has been observed with a number of other human cancer cell types in culture.

The present invention is designed to exploit HPR cytotoxicity against cancer cells. It is therefore preferred to formulate highly water soluble HPR using the free flowing lipid nanosystems described herein without eliminating the drug's natural cytotoxic action.

Figure 4:
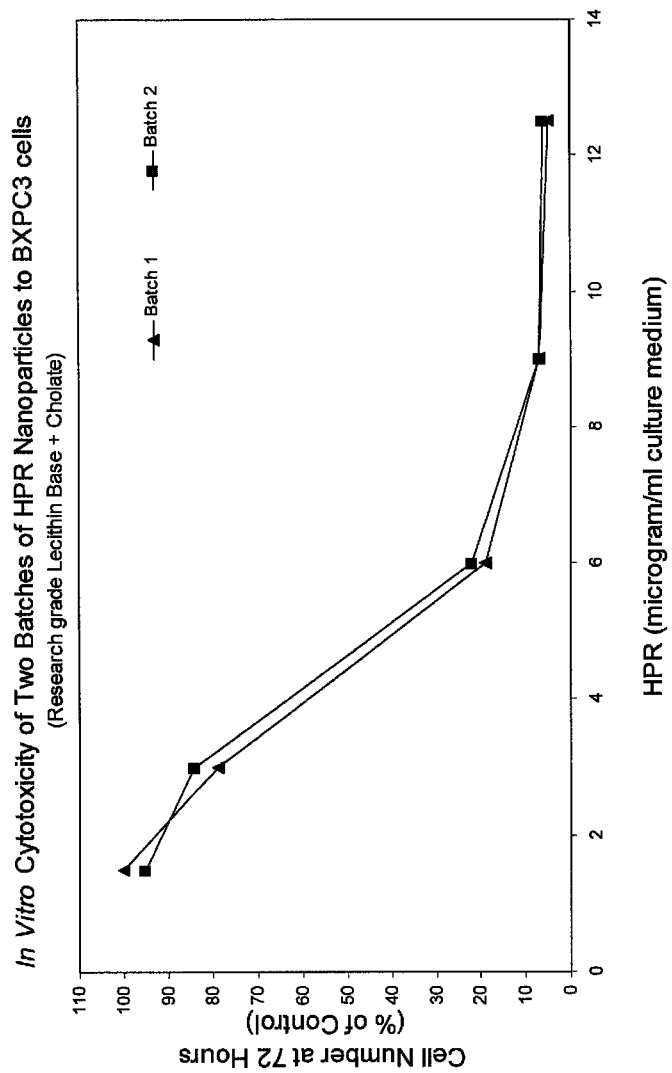
FIG. 4 is a graph showing the cytotoxicity in vitro of two batches of HPR nanoparticles against human pancreatic tumor cells of the BxPC3 cell line. Nanoparticles were made using a research grade lecithin base and sodium cholate.

Lipid nanosystem formulations of HPR as described herein were prepared and tested for cytotoxicity in vitro against BXPC3 human pancreatic cancer cells. Several formulations of highly water soluble HPR at 12.5 mg/ml, produced using lecithin-based systems containing either DMPC or cholate/cholic acid as describe above, retained cytotoxicity to human cancer cells in vitro, as shown in the FIG. 4 using the human pancreatic cancer cell line BXPC3.

The nanosystem formulations were prepared as described above using research grade or manufacturing grade lecithin from a number of different suppliers, and supplemented either with DMPC or cholic acid/cholate, and produced using scalable commercial methods for homogenization and membrane extrusion. HPR was cytotoxic when formulated as a lipid nanosystem using either specific research grade or specific cGMP grade lecithins. Control nanosystems prepared in the same way but excluding HPR were not cytotoxic.

BXPC3 cells are maintained in RPMI-1640 medium supplemented with 10% fetal bovine serum, 100 U/ml penicillin G, 100 μg/ml streptomycin and 1% L-glutamine in a humidified atmosphere of 95% air/5% $CO_2$ at 37° C. A confluent culture of BXCP3 cells in a 75 ml flask yields ≥1-1.5× $10^7$ cells. BXPC3 cells continue to grow over the single monolayer and do not undergo cell cycle arrest for approximately 24 hours after trypsinization and transfer to a new culture vessel, as long as the culture is seeded with at east 5000 cells/ml).

Cytotoxicity tests were initiated by seeding BXPC3 cells ($2.5 \times 10^4$ cells/ml) in 96-well flat bottom microtiter plates in a volume of 100 μl/well. Cells were re allowed to rest undisturbed for 24 hours before the addition of serial dilutions of HPR (lipid nanosystem formulation) at 20 μl per well into wells with 5 μg/ml gentamicin. Cells were incubated for 72 hours in the absence or presence of HPR (1.5, 3, 6, 9 or 12.5 μg/ml final concentrations). After 72 hours, the number of cells was assessed by uptake of the dye Alamar Blue (Biosource International, Camarillo, Calif.) added to each well at a 10% final concentration (10 μl/well). This non-toxic aqueous dye binds to cells in the microwells in proportion to the number of viable cells and acts as a monitor of metabolic activity (hence, viability) as a result of mitochondrial redox reactions during cellular growth/proliferation. Bound dye is quantified using fluorescent or visible light. Four control wells containing medium but no cells were included to determine background staining in the absence of cells. After two hours of incubation, color or fluorescence was read in an automated fluorimetric plate reader (Fluoroskan Ascent FL, Thermo-Form a Scientific, Marietta, Ohio). Excitation was set at 530 nm with emission at 590 nm. A standard curve was generated using manual cell counts vs arbitrary fluorescence units (AFU) generated by a two-fold serial dilution of control, untreated cells. AFU from the control wells (no HPR added), and the number of cells/well were calculated from this standard curve. Each sample was tested in quadruplicate (4 wells). Thus, the efficacy of each preparation was assessed by monitoring the growth rate of these cells after 72 hr exposure to varying concentrations of HPR. Cytotoxicity is expressed in the curves as the percentage of viable cells in the HPR-treated wells compared to the untreated control wells.

Figure 5:
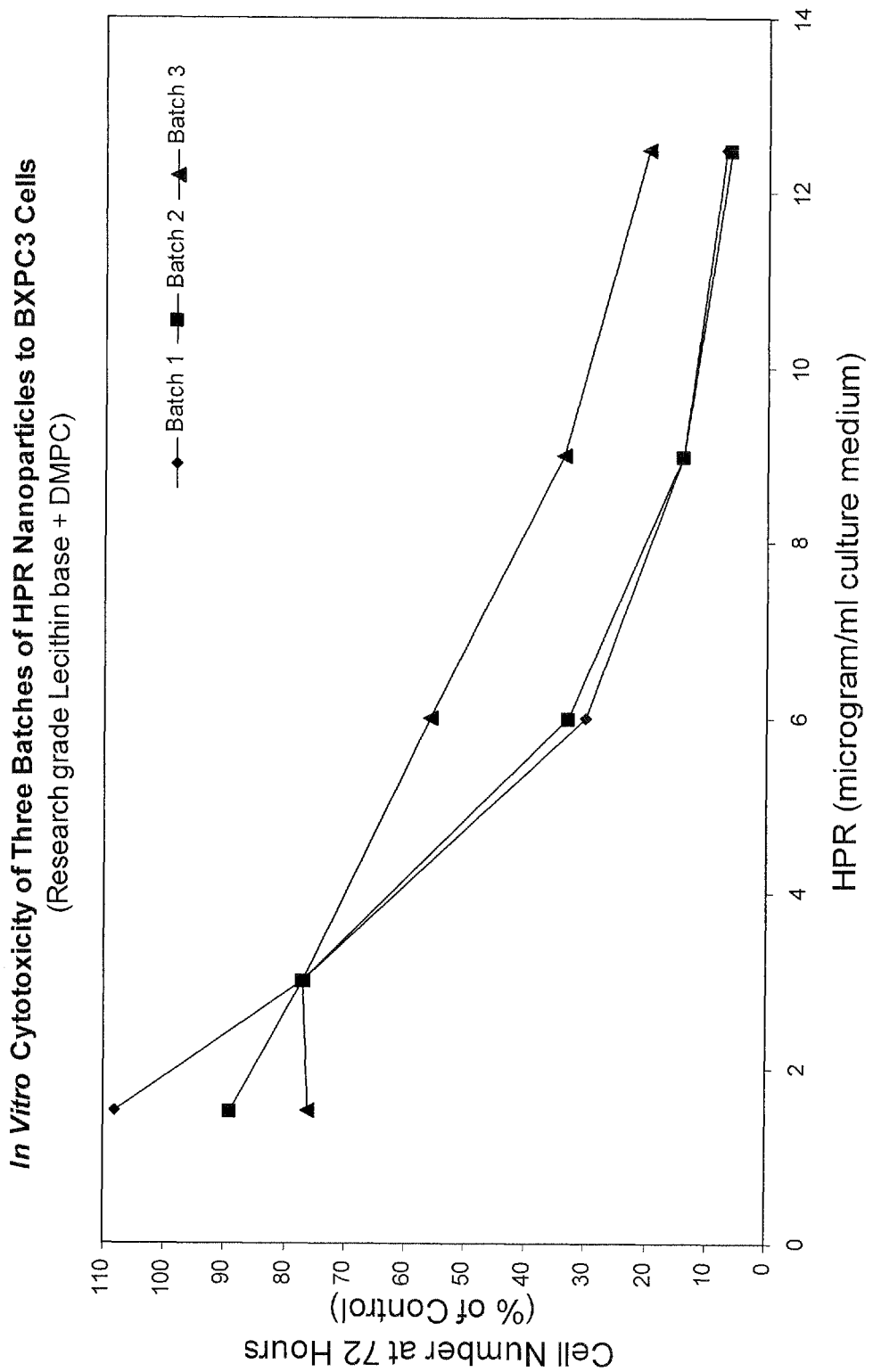
FIG. 5 is a graph showing the cytotoxicity in vitro against BxPC3 cells of two batches of HPR nanoparticles. Nanoparticles were made using research grade lecithin base and DMPC.
Figure 6:
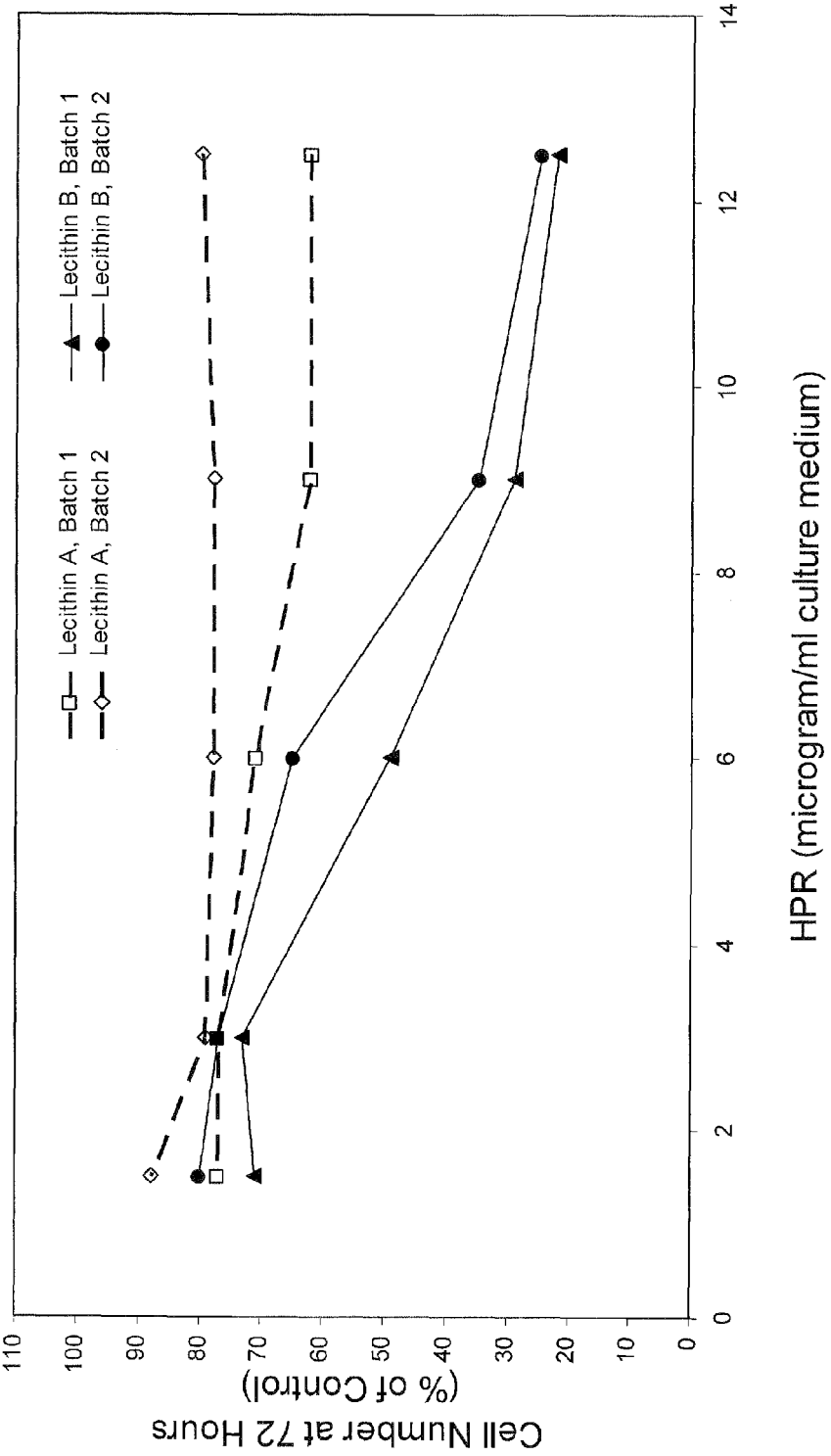
FIG. 6 is a graph showing the cytotoxicity in vitro against BxPC3 cells of two types of HPR nanoparticles. Nanoparticles were made using manufacturing grade lecithin base and DMPC.

For any particular formulation, the cytotoxicity of different preparations prepared on different days was very consistent, indicating not only the reliability of the assay but also consist biopharmacological properties the formulations. The results of several assays of different types of lipid nanosystem formulations are shown in the FIGS. 4-6.

It was concluded from the foregoing studies that these lipid nanosystems containing a neutral retinoid such as HPR would be cytotoxic against any of a number of human tumor cell types in vitro.

Figure 7:
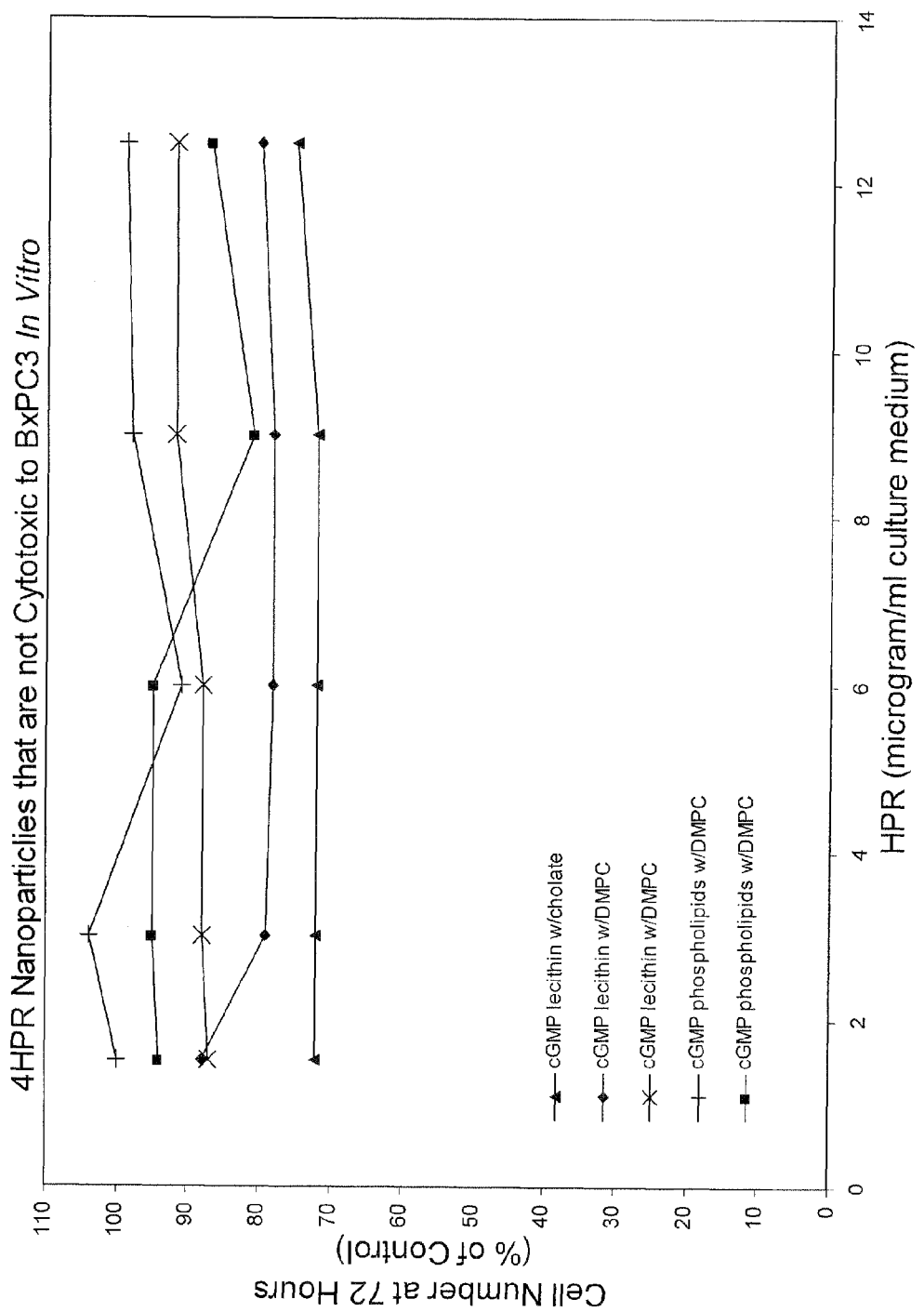
FIG. 7 is a graph showing the lack of cytotoxicity in vitro against BxPC3 cells of four batches of non-cytotoxic HPR nanoparticles.

In contrast to the foregoing results, it is also possible to prepare highly water soluble HPR in free flowing lipid nanosystems that are not cytotoxic in vitro, using different cGMP grade lecithins or chemically synthetic phospholipids as the lipid source. FIG. 7 shows results of cytotoxicity studies with illustrative HPR preparations that were not cytotoxic in vitro to BXPC3 tumor cells.

Example 8

Antitumor Activity of HPR Lipid Nanosystems In Vivo

Similar to the above findings, lipid nanosystems of highly water soluble HPR could be produced that were effective in treating tumors of human BXPC3 pancreatic carcinoma cells growing subcutaneously in immunocompromised mice. This is an accepted in vivo model for the cytotoxicity or other therapeutic action of an anti-cancer drug or treatment modality.+

By using different lecithin or phospholipids to produce the present lipid nanosystems, desired types and degrees of anti-tumor effects can be obtained. Some of these formulations are used to deliver HPR to tumors and other tissues and achieve a cytotoxic or chemotherapeutic effect. Others formulations made from other lecithin products and synthetic phospholipids are used to deliver non-cytotoxic HPR.

The former is formulations are designed for cancer chemotherapy, wherein toxic action on the tumor cells is the goal. Formulations that lack cytotoxicity is desirable for other medical applications including t differentiation therapy, retinoid therapy of non-malignant conditions, medical diagnostic imaging of HPR, or delivery of other materials that are incorporated into the lipid nanosystem during their production, as disclosed herein.

Figure 8:
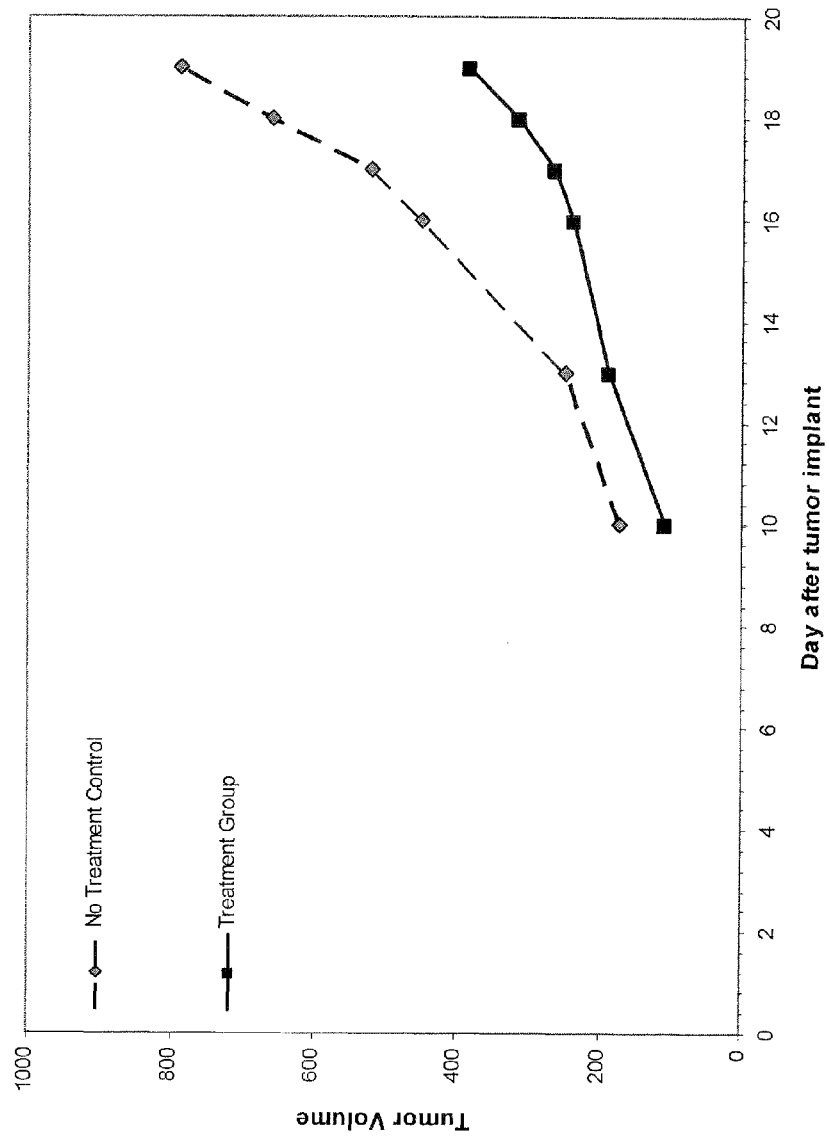
FIG. 8 is a graph showing the growth of BxPC3 tumors in immunocompromised mice treated with HPR nanoparticles made from research grade lecithin.

In the following example, a HPR formulation (F23) prepared fresh daily using research lecithin supplemented with cholate was administered as a bolus intravenous (IV) dose on alternate days into the tail veins of mice bearing subcutaneous xenografts of the human pancreatic cancer line BXPC3. Treatment was continued for seven doses of 300 mg/m$^2$/day (as 0.2 ml of a 12.5 mg/mL formulation). HPR treatment began on the $10^{th}$ day of tumor growth, when palpable tumors were present. The HPR formulation was well tolerated without toxicity or weight loss over 3 weeks of treatment. Tumor growth or its inhibition was determined based on tumor size assessed 3 times/week during the 3-week treatment period. Mean tumor size in control and treatment arms were compared, and statistical significance of differences was assessed using a grouped 'Student's t test. Results are shown in FIG. 8. The mean tumor size in the treated group was significantly lower (p<0.01) than the control group over days 16-19.

Figure 9:
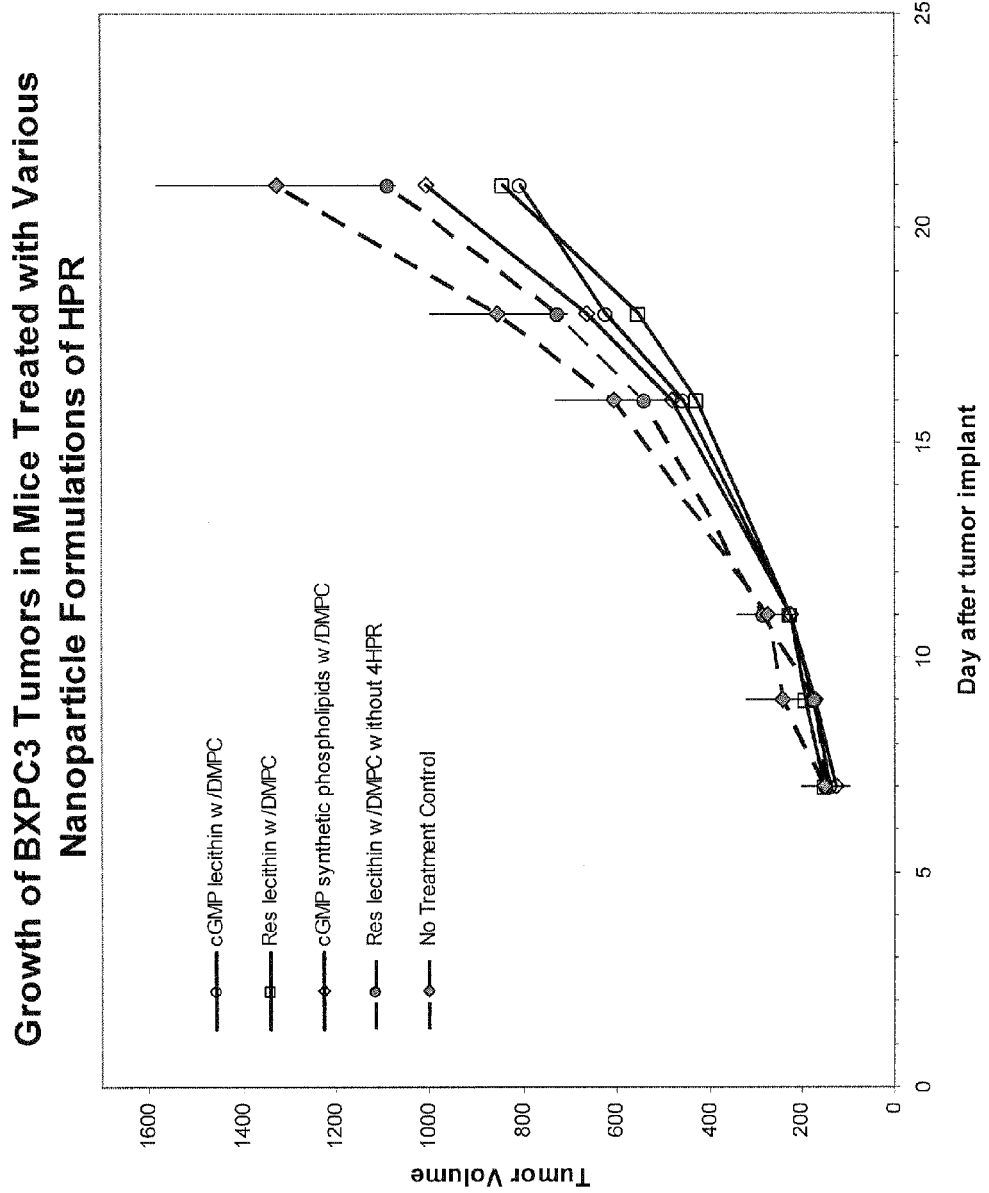
FIG. 9 is a graph showing the growth of BxPC3 tumors in immunocompromised mice treated with various HPR nanoparticle formulations.

In another example, HPR formulations prepared with either research grade lecithin or with manufacturing grade lecithin supplemented with DMPC were tested. Results are shown in FIG. 9. Eight doses of these formulations were administered on alternate days to groups of 7 mice. Attenuation of tumor growth was observed, starting on Day 7, at a dose level of 50 mg/kg (per injection). The HPR formulation prepared with manufacturing grade synthetic phospholipids supplemented with DMPC was did not inhibit tumor growth, the rate being similar to that of the group treated with a control preparation (research lecithin without HPR). The error bars shown in FIG. 9 indicate one standard deviation of the mean of the tumor volume of "no treatment control group.

Example 9

HPR Influx into Tumor Cells

Studies measuring the amount of HPR entering cultured BXPC3 cells over a 24 hr period ("influx studies") showed that various HPR formulations, whether or not they had cytotoxic activity, entered tumor cells in similar amounts. BXPC3 cells were maintained in culture as described above. After harvesting cells by trypsinization, cells were resuspended in medium and 5 ml containing $1.25 \times 10^6$ cells were seeded in 60 mm tissue culture dishes. The cells were allowed to incubate, undisturbed for 24 hours after which HPR was added at a final concentration of 12.5 µg/ml and the cells harvested 24 hours later. After removal from the incubator, medium containing HPR was removed. The adherent cells were then immediately washed with 1 ml cold PBS on ice and gently scraped from the dish in the presence of 1 ml cold PBS, after which they were dispersed by gentle continuous pipetting, counted and centrifuged for 30 seconds at 4° C. to pellet the cells. The pellet was resuspended in 1.0 ml acetonitrile containing BHT (4 µg/ml). Because the cells immediately clump in acetonitrile, they must be dispersed and counted while in PBS. Samples were stored at 4° C. until assessed for HPR content by HPLC analysis.

Results are reported in Table 10 below, which shows total HPR content per $10^6$ cells after 24 hrs.

TABLE 10

| HPR Content (µg per $10^6$ Cells) | | | | |
|---|---|---|---|---|
| Cytotoxic HPR Preparations (Research Grade Lecithins + cholate or DMPC) | | | Non-Cytotoxic HPR Preparations (synthetic phospholipids + DMPC) | |
| Cholate | 3.7 | 5.1 | 4.4 | 3.5 |
| Cholate | 1.4 | | 3.5 | 4.7 |
| DMPC | 4.4 | 5.6 | 4.3 | 3.5, 1.5 |
| | | | 3.0 | 1.2 |
| | | | 4.0 | 1.7 |

These measurements show that similar amounts of HPR in lipid nanosystem formulations were found associated with the cultured BXPC3 cells 72 hrs after treatment, irrespective of their cytotoxic activity. Therefore, the differences in cytotoxicity in vitro attributable to selection of lecithins or synthetic phospholipids for preparing the lipid nanosystem are not due to lack of HPR delivery into target cells. Thus, one need not be concerned with the cytotoxic activity of a formulation due to choice of lecithin or phospholipid base as a determinant of HPR delivery.

Example 10

HPR Selectivity for Pancreas and Other Tissues

HPR exhibits a natural propensity to accumulate in the pancreas among other tissues. This characteristic is at the foundation of the present embodiments directed to targeting HPR or other molecules associated with the nanoparticles in the formulation to the pancreas. Studies of HPR delivery to tissues in vivo were made 24-30 hours after a single intravenous injection of an HPR lipid nanosystem at a dose of 444 mg/m² into healthy rats or 300 mg/m² into immunocompromised mice, whether they harbored subcutaneous human tumor xenografts of the pancreas carcinoma line BXPC3 or PANC-1 or not. HPR was quantified in extracted homogenates of dissected tissue using HPLC methodology. The results appear in Table 11. The tissue contents were compared to results with lower doses in the scientific literature resulting from the intravenous injection of 30 mg HPR per cc ethanol at 30 mg/m² (as the higher doses achieved with the lipid nanosystems cannot be achieved using injection of the suboptimal formulation of ethanol-dissolved HPR).

TABLE 11

| | | Tissue Content of HPR After Intravenous Injection (µg HPR per gram of tissue wet weight) | | | | | |
|---|---|---|---|---|---|---|---|
| Formulation | Species/Tumor | | Plasma | Tumor (sc) | Pancreas | Liver | Kidney | Fat (Omentum) |
| Research grade lecithin + cholate (F23) | Mouse/BXPC3 | | 2.1 | 2.9 | 700 | 7.7 | 4.3 | 2.1 |
| | Mouse/(PANC-1) | 1 | 1.1 | 13.1 | 3.7 | 8.2 | 2.7 | 41 |
| | | 2 | 0.65 | 3.0 | 4.2 | 1.9 | 2.0 | 30 |
| | | 3 | 0.41 | — | 1.4 | 1.6 | 2.0 | 16 |
| | | 4 | 0.49 | 7.4 | 3.4 | 2.0 | 2.2 | 34 |
| Res lecithin w/cholate (F23) | Rat | | 4.5 | n/a | 21 | Not done | Not done | 51 |
| Ethanol[1] (not formulated) | Rat | | 0.094 | n/a | 0.98 | 1.8 | 2.2 | 0.94 |

[1] Swanson et al 1980.

The preferential delivery of HPR to the pancreas relative to the plasma is evident 24 hours after administration, indicating that these formulations continue to exhibit a key property of HPR—persistent retention in tissues of interest after delivery from the blood compartment. Comparison of results of lipid nanosystems compared to unformulated HPR dissolved in alcohol (last row) indicated that these formulations resulted in dramatically higher tissue content.

The results described above demonstrate the successful production of lipid nanosystems comprising the highly water insoluble neutral retinoid, HPR under cGMP and using as starting materials cGMP grade or manufacturing grade lecithins and chemically synthetic phospholipids. These nanoparticle formulations possess consistent degrees of in vitro cytotoxic activity (or absence of such activity. The property of in vitro cytotoxicity is correlated with antitumor activity against xenografted BXPC3 pancreatic carcinoma cells growing in mice.

This discovery illustrates a fundamental property of the plant-derived (vs. animal-derived) lipid nanosystems described herein—that specific formulations of certain desirable pharmaceutical properties can be reliably produced for specific medical applications and uses. Cytotoxic formulations are prepared for use in medical applications where cytotoxicity in vivo is desired, for example, cancer therapy and cytotoxic therapy for other proliferative disorders. Formulations that are not cytotoxic are prepared for medical applications where cytotoxicity in vivo is not desired, for example, delivery of neutral retinoids such as HPR or other therapeutic agents, recombinant DNA products (e.g., gene therapy, DNA vaccines), imaging agents (contrast agents, radioactive materials, etc.) to non-cancerous pancreatic tissue or to other tissues. This approach improves the availability, performance and utility of such materials other than HPR.

Example 11

Preparation of HPR Emulsions

A lipid may be comprised in an emulsion. A lipid emulsion is a substantially permanent heterogeneous liquid mixture of two or more liquids that do not normally dissolve in each other, by mechanical agitation or by small amounts of additional substances known as emulsifiers. Methods for preparing lipid emulsions and adding additional components are well known in the art (e.g., *Modern Pharmaceutics*, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

Thirty-one formulation experiments were performed to identify important variables and steps in the preparation of stable lipid emulsions prepared from HPR and USP ingredients. a plant-derived lecithin, soybean oil, glycerin, EtOH, Water USP and BHT. Glycerin was used to maintain isotonicity.

Key to preparing of HPR emulsions is the addition of the glycerin from the water phase, because glycerin added from within the oil phase precipitates the HPR. In addition, the preferred organic solvent for solubilizing and introducing HPR into the preparation is ethanol because it avoids precipitating the HPR. BHT serves to stabilize the HPR at the 50-60° C. temperatures required to prepare the oil phase for introduction into the aqueous phase. Also important in preparing emulsions, the warmed oil phase is introduced into the water phase at ambient temperatures of 20-28° C. Using a warm water phase instead failed to yield a stable emulsion. Also important is to avoid using either cholesterol or tocopherols.

Most preferred emulsions result from decreasing lipid fluidity by composition and/or lowering temperatures of the water phase and the mixing step after adding the oil phase.

A typical emulsion contained soluble HPR at 6 mg/ml. HPR solubility was tested by filtration through Isopore polycarbonate membranes with 0.4 µm pore size and >98% of the HPR was recovered after filtration of freshly prepared emulsions. Emulsions containing 18 mg/ml HPR could not be filtered through even the 1.2 µm pore size filter. Thus, preferred HPR concentrations solubilized using the emulsion strategy is 6-18 mg/ml

TABLE 12

Membrane Pore Size Affects HPR Filterability in Emulsions

| Pore size | % Recovery of HPR | mg drug adsorbed to membrane |
|---|---|---|
| None (control) | 100 ± 0.5 | — |
| 0.2 µm GTTP | Retained | — |
| 0.4 µm HTTP | 98.9 ± 2.0 | 0.014 ± 0.002 |
| 0.6 µm DTTP | 99.9 ± 0.9 | 0.020 ± 0.002 |
| 0.8 µm ATTP | 97.3 ± 0.4 | 0.020 ± 0.000 |
| 1.2 µm RTTP | 101 ± 0.9 | 0.016 ± 0.005 |
| Nutrivex ® In-Line filter | >98% | — |

Chemical analysis by HPLC showed that the HPR content in filtered HPR emulsions was stable for 3 months when stored in the dark at ambient room temperatures. HPR content was also stable under these conditions for 1 week after dilution with 50 parts 5% Dextrose USP or 0.9% Saline USP. On day 7 of storage under ambient room temperature, the median globule size was 3.7 µm (the 90% range was 2.22-6.17 µm) and the mean zeta potential was −43.2 millivolts.

Example 13

Preparation of Solid Dispersions

Solid dispersion is a technique in which the drug crystal lattice is disrupted by encapsulating into hydrophilic carrier molecules. As a consequence, the solubility and dissolution rate of the enclosed drug will be enhanced significantly. Solid dispersions have been extensively investigated as a means of enhancing drug solubility (Sekiguchi et al., 1961; Chiou et al., 1971; Mummaneni et al, 1990 and Du and Vasavada, 1993). Hydrophilic carriers like xylitol, polyvinylpyrrolidone, polyvinyl alcohol, polyethylene glycol etc. are used extensively in the formulation of many commercially available tablet and capsule preparations. Kollidon® 12 PF, Kollidon® 17 PF, Kollidon® 25 PF (BASF Corporation) and PEG 8000 (Union Carbide) were tested.

To evaluate the enhancement of HPR solubility, it was dissolved in a small amount (e.g. 4.5 mL) of ethanol in a round bottom flask and 0.5 mL of 40 ng/mL of BHT was added. Hydrophilic matrix (PEG 8000 or PVP) was separately dissolved in 5 mL of ethanol and added to the HPR solution. Ethanol was slowly evaporated under vacuum using Rota evaporator at 37° C. The solid dispersions were stored in a dessicator until evaluation of solubility.

The solubility enhancement effect of the solid dispersion was studied by dissolving the solid dispersion equivalent to 20 mg of drug in 4 mL of 0.1% ascorbic acid in water and allowing it about 24 hrs to reach equilibrium. The material was then centrifuged and filtered (PRO-XTM, 0.45 μm Hydrophilic Nylon membranes). The filtrate was appropriately diluted and analyzed by HPLC to quantify the amount of filterable HPR in the formulation.

The results of these studies (Table 13) showed that PEG8000 did not enhance HPR solubility significantly, whereas PVP increased the aqueous solubility, which was proportional to the molecular weight of PVP used. Among various sized PVP polymers, K25 increased the aqueous solubility of HPR dramatically, and K30 increased solubility as well. Higher PVP concentrations increased the aqueous solubility of HPR. PVP K25 at a drug:polymer ratio of 1:40 promoted the greatest solubility. However, the aqueous solutions of PVP25 at 1:40 drug:polymer ratio were very viscous and practically impossible to filter, foreshadowing a potential manufacturing problem upon scale-up. Based on these data, PVP K25 at some drug:polymer ratio below 1:40 was selected as a preferred formulation. PVP K25 at 1:20 drug:polymer ratio surprisingly showed the highest solubility, and was selected as the lead preparation under the solid dispersion strategy.

TABLE 13

Solubility of HPR in Solid Dispersions

| Polymer Grade | Drug:Polymer Ratio | HPR Conc. (μg/ml) |
|---|---|---|
| PEG 8000 | 1:10 | 0.20 |
| | 1:20 | 0.24 |
| | 1:30 | 0.34 |
| | 1:40 | 0.33 |
| PVP K12 | 1:5 | 245.70 |
| | 1:10 | 620.70 |
| | 1:20 | 2994.30 |
| PVP K17 | 1:2 | 54.27 |
| | 1:4 | 107.46 |
| | 1:10 | 333.74 |
| PVP K25 | 1:2 | 423.66 |
| | 1:4 | 274.37 |
| | 1:10 | 2137.04 |

Since PVP K25 increased the aqueous solubility of HPR dramatically, this polymer was further investigated at higher drug: polymer ratios along with PVP K30 from two different vendors. The solubility data shown in Table 14 confirmed that higher PVP concentrations increased the aqueous solubility of HPR, and PVP K25 at 1:40 drug:polymer ratio yielded the highest solubility.

TABLE 14

Solubility of HPR

| Formulation | Drug:Polymer Ratio | Mean ± S.D (μg) |
|---|---|---|
| PVP K25 | 1:10 | 2406.3 ± 199.8 |
| PVP K25 | 1:20 | 2639.0 ± 628.1 |
| PVP K25 | 1:40 | 3304.7 ± 214.8 |
| PVP K30 | 1:10 | 2955.4 ± 605.9 |
| PVP K30 | 1:20 | 2968.6 ± 115.7 |

TABLE 14-continued

Solubility of HPR

| Formulation | Drug:Polymer Ratio | Mean ± S.D (μg) |
|---|---|---|
| PVP K30 | 1:40 | 3280.2 ± 1286.6 |
| PVP K30* | 1:40 | 3280.2 ± 1286.6 |

PVPK30* is Polyvinylpyrrolidone, MW 30,000 from ISP and the other PVPs were obtained from BASF Corp.

Example 13

Modeling of Pharmaceutical Properties of Prototype Topical Products of Fenretinide Using Reconstituted Human Epidermis and Full-Thickness Skin Three useful topical compositions of HPR are described in Table 15, below and are denoted as C1, C2 and C5. They were prepared in the same way by first dissolving the HPR into the required volume of ethanol containing the BHT, where it is soluble. Then, the parabens were dissolved into the EtOH-HPR-BHT using a mixing method such as stirring. Next, the lipids, oils, surfactants and glycerin were added and dissolved by sonication with periodic mixing. The half of the required amount of water that also contained the indicated mass of pH determinants such as the KOH and trolamine was added and the preparation mixed. Then the remaining water was added to the indicated final weight of the preparation, followed by additional mixing. These materials can be stored in brown glass bottles in the dark under ambient laboratory temperatures for at least 1 month with no change in HPR content or deterioration of physical appearance and consistency.

TABLE 15

| | Topical composition | | |
|---|---|---|---|
| Ingredient | C1 | C2 | C5 |
| HPR (mg) | 50 | 25 | 20 |
| Stearic acid (g) | 6 | — | 24 |
| Stearyl alcohol (g) | 0.5 | — | 0.2 |
| Cetyl alcohol (g) | 0.5 | — | 0.2 |
| Sesame oil (g) | — | 5 | — |
| BHT (mg) | 2.5 | 1.25 | 1 |
| Glycerin (g) | 5 | 2.5 | 2 |
| Methyl Paraben (mg) | 50 | — | 20 |
| Propyl Paraben (mg) | 25 | — | 10 |
| KOH (g) | 0.45 | — | — |
| Trolamine (g) | — | — | 0.5 |
| Span 60 (g) | — | 0.625 | — |
| Tween80 (g) | — | 0.625 | — |
| Ethanol (mL) | 0.5 | 0.25 | 0.2 |
| Dist. Water up to g. | 50 | 25 | 20 |

Another topical preparation of HPR, designated PD05057 was prepared using a cGMP grade lecithin. A topical preparation of HPR can be prepared using a pharmaceutical grade of hydrogenated soy lecithin. This preparation is made by combining a lipid phase and an aqueous phase, separately made, followed by mixing. This preparation was made by combining a lipid phase and an aqueous phase, separately made, followed by mixing. This composition is summarized in Table 16.

TABLE 16

PD05057 Composition

| Ingredient | Weight (g) | % w/w |
|---|---|---|
| Benzyl Alcohol, NF | 60 | 2 |
| Isopropyl Myristate, NF | 240 | 8 |
| Cholesterol, USP | 9 | 0.3 |
| Fenretinide | 3 | 0.1 |
| Propylene Glycol, USP (part A) | 300 | 10 |
| Vitamin E Acetate, USP | 9 | 0.3 |
| Polysorbate 80, USP | 22.5 | 0.75 |
| Phospholipon 90H | 90 | 3 |
| BHT, NF | 3 | 0.1 |
| Purified Water (part A) | 840 | 28 |
| Carbopol 980, NF | 12 | 0.4 |
| Edetate Disodium, USP | 3 | 0.1 |
| Triethanolamine 99% | 7.5 | 0.25 |
| Propylene Glycol, USP (part B) | 300 | 10 |
| Purified Water (part B) | 1101 | 36.7 |
| TOTAL | 3000 | 100 |

To prepare the lipid phase, 900 g of purified water was heated to 65° C. The following oil phase materials were melted by mixing in a mix can, isopropyl myristate, cholesterol, vitamin E acetate, Polysorbate 80, BHT, hydrogenated soy lecithin, and propylene glycol. Next, HPR was mixed with benzyl alcohol at room temperature, and the mixture heated to 60° C. in a water bath. Once it reached temperature, it was added to the melted lipid phase followed by mixing for 10 minutes and its temperature maintained at 55° C.-65° C. During this time, the weight of the water was adjusted to 840 g, and its temperature maintained at 55° C.-65° C. The water was then added to the lipid phase and mixed for 5 additional minutes, while maintaining the temperature at 55° C.-65° C. After mixing, the temperature was reduced to 20° C. in 5° C. increments over 30 minutes.

To prepare the aqueous phase, 1100 grams of water and then 300 gram propylene glycol were added to a stainless steel container and mixed at 400 rpm in a Lightnin mixer. Then, disodium EDTA was added to the stainless steel container and allowed to dissolve while mixing. Next, carbomer was added to the stainless steel container slowly, while continuing stirring to a uniform and lump-free dispersion. The carbomer dispersion was transferred to a mix can and mixed for 10 minutes. After adding trolamine diluted with water.

To prepare the HPR product, the lipid phase was introduced into the aqueous phase and mixed. The resulting product was air bubble-free, smooth gel with no crystals.

An initial study using isolated epidermis and full-thickness cadaveric skin mounted in Franz cells found that four topical formulations of fenretinide (HPR) of which three are shown in Table 15 (C1, C2, and C5) permeated the epidermal surface.

Within 3 hours of application of any of these formulations, HPR levels were achieved in the epidermis that exceeded the therapeutic level that induces apoptosis in malignant cells after 72 hours, which is >4 µg/gram tissue wet weight. Epidermal drug levels achieved by 3 hours were stable to 24 hours. The C5 formulation reached 11. µg/mg after single application. The products were tested as 0.1% strength creams. Thus, by increasing strength of the product to 0.5% and applying twice daily, it is possible to achieve target content levels in the skin. Moreover, as discussed below, the C5 formulation may be advantageous in reaching this level in epidermis alone.

When the same formulations were tested on full-thickness cadaveric skin (epidermis+dermis), drug levels were lower per gram of tissue wet weight than when isolated epidermis was tested, but nevertheless therapeutic levels were reached in the full-thickness specimens 24 hours after application. C2 permeated full-thickness skin more rapidly than C1 and C5. C2 delivered maximum drug by 3 hours and maintained these levels for 24 hours; in contrast, maximum HPR levels in full-thickness skin were not reached until 24 hours after applying C1 or C5. Considering the pharmaceutical goal of delivering HPR to the epidermis while minimizing systemic exposure by minimizing flux through the skin, C5 showed the most favorable disposition profile. It reached maximum and stable levels in the epidermis within 3 hours, but at this time point had reached only ~50% of its maximum level in intact skin found at 24 hours. Therefore, among the formulations showing rapid deposition of HPR in epidermis, flux through epidermis was slowest using the C5 preparation.

One technical difficulty in measuring HPR flux through skin specimens ex vivo is creating meaningful sink conditions in the receiver medium of the Franz cell. HPR is poorly soluble in physiological saline (~5 ng/mL) typically used as receiving media in Franz cell experiments. As a result, it is unlikely that 10 ml of typical receiver medium creates sink conditions (50 ng is the maximum drug solubilized). Without sink conditions to mimic the contributions of dermal circulation and systemic elimination to local clearance of topical drugs in vivo, the in vitro HPR flux might be underestimated.

In the above study, epidermal flux was measured a second time using receiver medium composed of phosphate-buffered saline supplemented with ethanol to 20 vol %, which increases HPR solubility by 200-fold to ~1.3 µg/mL and receiver chamber capacity to ~13 µg. Unexpectedly, adding ethanol to 20% slightly increased HPR permeation into isolated epidermis over PBS alone, but HPR was still not detected in the receiver medium. This result indicated that HPR has affinity for the epidermis in cadaveric specimens under sink conditions.

This finding further emphasizes the natural insolubility of HPR without lipid formulations, even in 20% ethanol in aqueous the HPR, and shows the dramatic effect of the present formulations on the maximum water content of HPR that behaves as if it were in solution.

The reconstituted skin system is ideally suited for such a study because physiological interactions between the epidermis and dermis are naturally integrated into the system. So, the release of several pro-inflammatory cytokines in response to topical exposure to C5 and several approved products of varying irritancy was compared. The influence of co-exposure to C5 upon pro-inflammatory topical products for AK was also explored to provide data for considering the potential for a combination product that exploits the anti-inflammatory action of HPR to improve safety and compliance over current APIs. These experiments were also conducted using EpiDerm-606X skin model, which is an organotypic, barrier-enhanced in vitro testing system approved for assessing dermal corrosivity by both US (NTP/ICCVAM) and EU regulators (OECD/ECVAM).

Methods

Analytical HPLC.

Using an analytical method measuring HPR by HPLC, and extraction procedures that yield >95% recovery of HPR from skin homogenates, EpiDerm Enhanced Barrier Function and EpiDerm Full-thickness skin specimens were removed from the Franz cells at the scheduled time, washed and halved as described below, and then homogenized and extracted in acetonitrile supplemented with 4 µg/mL BHT, 0.1% ethanol for quantitation of HPR by HPLC. Receiver medium specimens were collected and processed for HPR analysis by HPLC as described below. Injection volumes were 100 µl for extracts of skin and receiver medium and 50 µl for calibration standards. HPR quantitation was by back calculation to a standard curve constructed from clinical grade HPR received from the NCI. Quantitation of all-trans-retinoic acid (ATRA) in Retin-A 0.1% utilized a detector response coefficient derived from the analysis of Retin-A cream, wherein 1.05 µg ATRA eluting at 16.9 minutes in the HPLC method yielded a detector peak area of 5659 mAU at 365 nm, or 5,389 mAU/µg drug. When applied to potency analysis of triplicate samples of Retin-A, this method of quantitation returned findings of 98.3%, 105.4% and 109.5% of label strength (104±6%). A similar analysis of HPR cream #PD05057 from the testing lab returned findings of 124.4%, 121.6%, and 135.7% of label strength for a 0.1% gel (127±7%). For the second permeation study of Retin-A, PD05057 and HPR formulation C5 2005 using enhanced barrier function epidermal models, ATRA in the extracts of treated skin was quantified against an ATRA standard curve and HPR against an HPR standard curve. The sample labeled "PD05057, 0.1% HPR Gel (40 C for 1 Month)" was also analyzed and found to contain 129±7% of label strength, and the similar potency compared to material stored under ambient conditions indicated that the HPR in the laboratory's product was stable under accelerated storage conditions for 1 month. However, this accelerated storage sample was not used in the reconstituted skin systems.

Determination of Saturation Solubility of HPR in the Presence of Physiological Concentrations of Human Drug Binding Plasma Proteins.

Purified human proteins were obtained from Sigma Chemical Company and dissolved in receiver medium, which was the same as the specialized medium from Mattek Inc used to maintain reconstituted skin systems or assay enhanced barrier permeability function. The individual proteins were dissolved to their respective plasma concentrations: high-density lipoprotein to 0.2 mg/mL, retinol binding protein to 0.05 mg/mL, serum albumin to 50 mg/mL (A6909, lot #055K8904), and acid α1-glycoprotein to 1 mg/mL (50646, lot #448248/1). HPR dissolved to 100 mg/mL in absolute ethanol supplemented with 4 mg/mL BHT was added to each protein solution to final theoretical concentration of 50 µg/mL and mixed by vortexing, the insoluble drug removed by centrifugation (12,000×g, 5 min, 23° C.), and the supernatant analyzed by HPLC to quantify HPR concentration.

Cultivation of Reconstituted Skin Specimens.

18 reconstituted EpiDerm-Full Thickness specimens (EFT-306-AFAB-PRF, lot #7024-306-AFAB-PR) and 18 reconstituted EpiDerm Skin Model Enhanced Barrier Function (EPI-606-X-AFAB-PRF, lot #5093ofs) were received in good condition from Mattek Inc via overnight courier. Epi-Derm-FT was maintained in culture by specialized medium changes every other day according to the manufacturer's instructions. EpiDerm-606X was stored refrigerated until use. EpiDerm-FT medium was free of phenol red, antibiotic and anti-fungal additives (EFT-300-MM-ASY-AFAB-PRF, lot #110405aab and EPI-100-X), so as to avoid creating artifactual toxicity or proinflammatory response. The particular skin specimens were all reconstituted with normal human epidermal keratinocytes and, for EpiDerm-FT, fibroblasts as well from a single donor foreskin. Mattek has archived additional frozen aliquots of this NHEK preparation, as well as from one additional foreskin donor. EpiDerm reconstituted with breast keratinocytes is also available from other donors upon request.

Assay of Delivered Dose and Retinoid Flux through EpiDerm Full-Thickness Skin and EpiDerm Barrier Enhanced Specimens Three topical products were tested in the in vitro skin model: Retin-A 0.1% (lot #5BM258, expiry 02/07), HPR in topical formulation C5 and another HPR formulation (PD05057). These drugs were tested blindly using the following codes: "A" for Retin-A, "B" for the C5 formulation of HPR, and "D" for the HPR formulation PD05057. Receiver medium was made by mixing pre-warmed, 37° C. EFT-306 medium 5:1 with human serum albumin (Sigma A6909, lot #055K8904, then lot #095K8906) to its physiological concentration of 50 mg/mL. To prevent oxidation of HPR during the collection period, BHT was added to the receiver medium to a final concentration of 10 µg/mL from a 40 mg/mL solution of BHT-NF (Spectrum Chemicals, B1196, lot #UM0659) in Ethanol USP (NDC 11098-503-05, lot #121310). Each sterile amber Franz cells was pre-warmed to 37° C. using a circulating water bath, the bottom chamber filled completely with receiver medium (~10 ml), and then reconstituted skin specimens were removed from the cell culture wells and spread across the orifice epidermis upward, and clamped into place with a sterile top chamber. Pre-weighed aliquots of a target dose of 1.7 mg Retin-A prepared using an analytical balance were applied to the epidermal face, disbursed and messaged with the aid of the rubber tip of 1 ml BD tuberculin syringes and the start time recorded. At each experimental time point (0, 2, 3, 4, 5 hours after application of drug product), the designated skin sample was removed from the Franz cell, washed rapidly twice in receiver medium, the excess margins which were not treated with cream trimmed away, and the 1 cm$^2$ treated specimen area sliced into two equal halves (labeled with time and "5"). One-half was submitted for homogenization in 0.5 ml HPLC grade acetonitrile containing 4 µg/mL BHT, and the second half placed in a labeled cassette in neutral buffered formalin (KCl Pathology Core), fixed and embedded in paraffin for archiving. Then, a 2 ml sample of receiver medium was withdrawn (labeled with time and "M"), and 1 ml was stored at 4° C. and 1 ml was extracted for HPLC analysis by adding 1:1 HPLC grade acetonitrile supplemented with 4 µg/mL BHT.

This EpiDerm-FT study was repeated using C5 and PD05057 formulations, and subsequently the entire study was repeated with Retin-A, C5 and PD05057 using the Epi-Derm-606X Enhanced Barrier Function model.

Results

Establishing Physiologically-Relevant Sink Conditions in the Franz Cell Receiver Fluid for Studying Drug Permeation.

Transdermal flux studies of topical products in Franz cells are best performed under sink conditions in the receiver chamber, which closely reflect the in vivo situation where dermal circulation and systemic metabolism eliminate drug from the dermal side of the skin and establish the theoretical maximum concentration gradient that drives drug flux. However, HPR is poorly soluble in aqueous systems (~5 ng/mL), so it is difficult to establish sink conditions using physiological buffers. The previous study of HPR flux through cadaveric epidermis utilized buffers containing 20% ethanol in the receiving chamber (1.3 µg/mL), but high organic content was not suitable for the current study where living tissue was being tested. Instead, SciTech desired to create sink conditions for the permeation studies by supplementing receiver fluid with physiologically-relevant drug binding proteins rather than organic solvents.

A study of the HPR solubilizing properties of physiological concentrations of four human drug-binding plasma proteins that were expected to bind HPR under physiological conditions was conducted in receiver medium: high-density lipoprotein (HDL), retinol binding protein (RBP), albumin (ALB), and acid α-1-glycoprotein (AGP). Although certainly not the highest affinity binding, ALB solubilized more HPR per mL of receiver medium than any other plasma protein tested, driven primarily by its much higher physiological concentration than the other proteins. The solubilizing capacity of ALB was 7.5 μg HPR per ml of medium, which was 5-fold higher than that of 20 vol % ethanol. Using physiological concentrations of ALB in the 10 ml receiving medium chamber created a sink condition capable of binding 75 μg of HPR. Since the test surface area of the Franz cell was 1 cm$^2$ and the testing was conducted over 5 hours, this receiver medium was capable of supporting an average flux rate of 15 μg/cm$^2$/hour. It was concluded that this receiving medium should provide true sink conditions, considering the applied test dose of API from each formulation was just 1.7 μg/cm$^2$.

Disposition of All-trans-Retinoic Acid in EpiDerm-FT.

Retin-A was the first product tested in the reconstituted skin system to provide a frame of reference for the evaluation of HPR products. The actual confirmed dose of Retin-A applied to each 1.0 cm$^2$ of skin in the specimens was 1.95 μg±0.06 μg (3.0% CV), and the confirmed time points of specimen collection were 0.2, 2.05, 3.0 and 5.0 hours after product application. HPLC analysis of 52.2 mg product extracted with 4.95 ml acetonitrile/BHT revealed the presence of two retinoids—a major peak at 16.9 minutes eluting with ATRA and a minor peak at 14.1 minutes eluting with 13-cis-retnoic acid. Based on quantitation at 365 nm, the ATRA represented 85% of the retinoid substance in the preparation.

ATRA was detected in the EpiDerm-FT specimen within 0.2 hours of application, and rose to 0.056 μg by 3 hours (2.9% of the applied dose of 1.95 μg) and then slowly declined with t½>2 hours. No ATRA was detected in the receiver medium at baseline or over the 5 hour collection period. In contrast, the contaminating retinoid in Retin-A (13-cis-RA) permeated the EpiDerm-FT specimen much more rapidly and its levels were already declining by 2 hours. Consistent with its more rapid skin permeation than ATRA, the substance accumulated in the receiver medium by the 5 hour time point. Since a peak concentration was not detected during the sampling time frame, the data cannot exclude the possibility that this substance was rapidly delivered into the skin to maximum levels within 0.2 hours. However, it seems more likely that the absorbed dose would have peaked between 0.2-2 hours and that the timing of the sampling missed the peak level, based on the first appearance of the substance in the receiver medium at 5 hours. Studies of HPR creams proved that the ATRA and the contaminating substance were derived from the Retin-A product (see next section).

Comparison of C5-Derived HPR and Retin-A Derived ATRA Disposition in the EpiDerm-FT Model The C5 formulation of the present invention was tested in the EpiDerm-FT system, so the disposition of its HPR component could be compared to that of the reference compound in Retin-A, ATRA and eventually used for comparison to PD05057 (see Table 15). The actual confirmed dose of HPR applied to each 1.0 cm$^2$ of skin in the specimens was 2.2 μg, and the confirmed time points of specimen collection were 1.0 and 3.0 hours after product application. HPLC quantitation of HPR was based on back extrapolation to a calibration curve prepare with clinical grade HPR from the NCI.

HPR was detected in the EpiDerm-FT specimen within 1 hour of application at 0.032 μg, and rose to 0.091 μg by 3 hours. The permeation of 4.1% of the applied dose by 3 hours after application compares favorably to the performance of ATRA form Retin-A. The rate of HPR permeation into the EpiDerm FT specimens was similar to that of ATRA, and like ATRA, no HPR was detected in the receiver medium at either time point. No ATRA or cis-RA was detected in EpiDerm-FT specimens exposed to HPR, consistent with the lack of these substances in the HPR API source. Negative findings for these two materials also prove that the ATRA and contaminating retinoid (probably 13-cis-RA) found in the skin specimens during the evaluation of Retin-A were derived from the applied cream, and were not endogenous materials. Since the HPR content was still rising at 3 hours but it was not detectable in the receiver medium, the study of HPR permeation from the PD05057 preparation added the 5 hour time point to determine if HPR levels were still rising at this point or start to decline around 3 hours.

Comparison of Disposition of PD05057-Derived HPR, C5-Derived HPR and the ATRA Reference Compound from Retin-A in the EpiDerm-FT Model.

The PD05057 formulation was subjected to a more detailed time course study of HPR permeation into EpiDerm-FT (Table 15). The mean applied dose was 2.1 μg of HPR. This study confirmed maximum HPR levels were reached 3 hours after application and had begun to decline by 5 hours after application. At 3 hours, skin levels of HPR had reached 0.27 μg, which represents 13% of the applied dose. This peak level was ~3-fold higher than achieved with C5, which may be explained by the liposomal base of the other formulation. Previous studies of the formulations of the present invention also found higher HPR levels in cadaveric skin using a liposomal formulation than the non-liposomal C1, C2 or C5 formulations. Using 100 mg as a rough approximation of wet tissue weight of the EpiDerm-FT disk, PD05057 delivered maximum levels of 2.7 μg per gram of tissue weight. This exposure level achieved with the 0.1% strength gel is close to the therapeutic target of 4 μg/gram that must be maintained for >72 hours to induce tumor cell apoptosis. A slightly higher strength gel applied twice per day should achieve target therapeutic levels in living full-thickness skin. The kinetics of permeation of HPR from PD05057 and of ATRA from Retin-A appear similar, although HPR reached higher levels in the skin than ATRA. Importantly, despite higher delivered dose to the reconstituted skin, HPR was not detectable in receiver medium at any of the time points out to 5 hours.

TABLE 17

DISPOSITION OF HPR AND ATRA IN EPIDERM-FT (FULL THICKNESS LIVING SKIN MODEL)

| | ATRA | | C5 | | PD05057 | |
|---|---|---|---|---|---|---|
| Hours | Medium μg | Cells μg | Medium μg | Cells μg | Medium μg | Cells μg |
| 0.2 | 0 | 0.031 | — | — | — | — |
| 1 | — | — | 0 | 0.032 | 0 | 0.127 |
| 2.1 | 0 | 0.042 | — | — | — | — |
| 2.3 | — | — | — | — | 0 | 0.133 |
| 3 | 0 | 0.056 | — | 0.091 | 0 | 0.269 |
| 5 | 0 | 0.035 | — | — | 0 | 0.203 |

Comparison of Retinoid Permeation in the Epidermal Model of Enhanced Barrier Function.

Retinoid permeation was compared at similar time points in reconstituted isolated epidermis cultured under conditions that enhance its permeability barrier function (EpiDerm-606X, Mattek, Inc.) (See Table 16). The early sampling time for the Retin-A study was moved to 1-hour. The average applied dose of cream or gel in this study was 2 mg. No endogenous retinoids were detected in the receiver medium or skin extracts at baseline just prior to application of the retinoid products. In this model system composed exclusively of epidermis on a membrane support, the permeation of HPR C5 was identical to that seen previously in the full-thickness skin model. In contrast, the permeation of both ATRA from Retin-A and HPR from PD05057 were much faster, consistent with much less barrier function in this model. It is possible that the absence of the dermal connective tissue leads to more fragile epidermal surfaces, which barrier function can be damaged by the physical application of the creams and gels. However, no retinoids were detected in the receiver medium at any time points, suggesting that the reconstituted epidermal tissue had not been damaged.

It is interesting that in the absence of functional dermis, the two clinical products showed similar and somewhat unfavorable epidermal permeation kinetics that were quite distinct from their kinetics in the EpiDerm-FT model. In contrast, the present invention's C5 formulation delivered identical levels of HPR over time in the EpiDerm-606X and EpiDerm-FT models. These data suggest that the clinical formulations drive rapid permeation of ATRA and HPR through the epidermis, which accumulates in the dermis or at the epidermal-dermal junction, whereas the SciTech formulation deposits HPR into the epidermis independent of dermis structure/function. It is conceivable that the different permeability of HPR from PD05057 and from the C5 formulation is due to an excipient that facilitates rapid epidermal penetration of retinoids which is not present in the C5 preparation. If so, then the C5 formulation offers distinct advantages in delivering and retaining HPR in the epidermis where disease processes occur. Of course, it is also possible that the presence of dermal tissue structure or function may modify the biological properties of the epidermis in the EpiDerm-FT model and create permeation properties more akin to normal skin in situ.

TABLE 18

DISPOSITION OF HPR AND ATRA IN EPIDERM-606X (EPIDERMAL MODEL)

| Hours | ATRA | | C5 | | PD05057 | |
|---|---|---|---|---|---|---|
| | Medium µg | Cells µg | Medium µg | Cells µg | Medium µg | Cells µg |
| 1 | 0 | 0.209 | 0 | 0.030 | — | 0.191 |
| 2 | 0 | 0.106 | — | — | 0 | 0.138 |
| 3 | 0 | 0.046 | 0 | 0.086 | — | 0.054 |
| 4 | — | — | — | — | — | — |
| 5 | 0 | 0.032 | — | — | 0 | 0.063 |

CONCLUSIONS

Pharmacologically relevant amounts of topical products (1.7 mg product) can be applied reproducibly to the EpiDerm models. The PD05057 HPR formulation delivered higher doses of HPR into full-thickness skin than the present C5 formulation, which reached putative therapeutic levels. The higher permeation of HPR from PD05057 confirmed previous findings with one of the present liposome-based formulations prepared for topical application.

In the presence of dermal structure/function, ATRA from Retin-A and HPR from PD05057 and HPR C5 showed similar permeation kinetics. Permeation of HPR from C5 was independent of the presence or absence of dermal tissue.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

The invention claimed is:

1. A lipid nanoparticle composition comprising a neutral retinoid in a phospholipid component, wherein
    (a) the nanoparticles have diameters of less than or equal to about 1000 nm;
    (b) the retinoid is integrated within the phospholipid component to a final retinoid concentration of between about 4 and about 75 mg/ml;
    (c) the phospholipid component is:
        (i) a plant lecithin acceptable for use in mammals in vivo;
        (ii) phospholipids of said lecithin of (i);
        (iii) cholic acid or a salt thereof and one or more synthetic, chemically-defined phospholipids having two fatty acid chains; or
        (iv) one or more synthetic chemically-defined phospholipids having two fatty acid chains; and
    (d) the nanoparticles have a surface charge characterized by a zeta potential of between about −50 millivolts to about +10 millivolts.

2. The lipid nanoparticle composition of claim 1 wherein the particles have diameters in the range of about 200 to about 1000 nm.

3. The lipid nanoparticle composition of claim 1 wherein the particles have diameters less than or equal to about 200 nm.

4. The lipid nanoparticle composition of claim 1 wherein the concentration of the retinoid is greater than or equal to 6 mg/ml.

5. The lipid nanoparticle composition of claim 1 wherein the retinoid is 4-hydroxyphenyl-retinamide (HPR).

6. The lipid nanoparticle composition claim 1 that comprises said synthetic phospholipids.

7. The lipid nanoparticle composition of claim 6 wherein the phospholipids are characterized in that
    (a) one or both fatty acid chains are saturated and consist of 16 or fewer carbon atoms; and/or
    (b) one or both fatty acid chains are unsaturated and consist of 18 or fewer carbon atoms.

8. The lipid nanoparticle composition of claim 7 wherein the synthetic chemically defined phospholipids comprise one or more of 1,2-dipalmitoyl-sn-3-phosphatidylcholine (DPPC), 1,2-dioleyl-sn-3-phosphatidylcholine (DOPC), 1,2-dimyristoyl-sn-3-phosphatidylcholine (DMPC) and 1,2-dimyristoyl-sn-3-phosphoglycerol (DMPG).

9. The lipid nanoparticle composition of claim 1 wherein said zeta potential range is achieved by combining two or more phospholipids having two fatty acid chains of less than or equal to 14 carbon atoms, wherein said two or more phospholipids comprise less than about 25% of the total phospholipid.

10. A pharmaceutical composition comprising the lipid nanoparticle composition of claim 1 for intravenous or other parenteral delivery of the neutral retinoid to a human subject in need thereof,
    which pharmaceutical composition is free of non-ionic surfactants, detergents, polyoxylated compounds, alkoxylated oils or any animal-derived substance known to be allergenic or to induce an anaphylactic reaction when administered to a human.

11. A pharmaceutical composition comprising the lipid nanoparticle composition of claim 5 for intravenous or other parenteral delivery of the HPR to a human subject in need thereof, which pharmaceutical composition is free of non-ionic surfactants, detergents, polyoxylated compounds, alkoxylated oils or any animal-derived substance known to be allergenic or to induce an anaphylactic reaction when administered to a human.

12. The lipid nanoparticle pharmaceutical composition of claim 10 characterized in that, after parenteral administration to a mammalian subject, the retinoid accumulates selectively in the pancreas resulting in a pancreatic concentration that is at least four-fold higher than the concentration of the retinoid in plasma.

13. The lipid nanoparticle pharmaceutical composition of claim 11 characterized in that, after parenteral administration to a mammalian subject, the HPR accumulates selectively in the pancreas resulting in a pancreatic concentration that is at least four-fold higher than the concentration of the retinoid or HPR in plasma.

14. The lipid nanoparticle composition of claim 5 comprising:
    (a) 5 to 75 mg/ml HPR;
    (b) 25 to 125 mg/ml DPPC;
    (c) 10 to 75 mg/ml DOPC;
    (d) 0 to 20 mg/ml DMPC;
    (e) 0 to 10 mg/ml DMPG;
    (f) 0.01 to 0.5 mg/ml hydroxytoluene (BHT); and
    (g) 1 to 10% v/v ethanol.

15. The lipid nanoparticle composition of claim 14, comprising:
    (a) 12.5 mg/ml HPR;
    (b) 64 mg/ml DPPC;
    (c) 25 mg/ml DOPC;
    (d) 4.14 mg/ml DMPC;
    (e) 0.76 mg/ml DMPG;
    (f) 0.02 mg/ml BHT; and
    (g) 1-10% v/v ethanol.

16. The lipid nanoparticle pharmaceutical composition of claim 11, comprising:
    (a) 5 to 75 mg/ml HPR;
    (b) 25 to 125 mg/ml DPPC;
    (c) 10 to 75 mg/ml DOPC;
    (d) 0 to 20 mg/ml DMPC;
    (e) 0 to 10 mg/ml DMPG;
    (f) 0.01 to 0.5 mg/ml BHT; and
    (g) 1 to 10% v/v ethanol.

17. The lipid nanoparticle pharmaceutical composition of claim 16, comprising:
    (a) 12.5 mg/ml HPR;
    (b) 64 mg/ml DPPC;
    (c) 25 mg/ml DOPC;
    (d) 4.14 mg/ml DMPC;
    (e) 0.76 mg/ml DMPG;
    (f) 0.02 mg/ml BHT; and
    (g) 1-10% v/v ethanol.

18. A method for producing the lipid nanoparticle composition of claim 1, comprising:
    (a) dissolving the retinoid, an antioxidant and a phospholipid component selected from the group consisting of
        (i) a plant lecithin acceptable for use in mammals in vivo;
        (ii) phospholipids of said lecithin of (i);
        (iii) cholic acid or a salt thereof and synthetic, chemically-defined phospholipids having two fatty acid chains; or
        (iv) synthetic chemically-defined phospholipids having two phospholipid chains, in a solvent or solvent mixture comprising an alcohol, a chlorinated organic solvent or both, thereby producing a solution that comprises the retinoid, an antioxidant, and lipid component in the alcohol and the chlorinated organic solvent;
    (b) evaporating said solvents under vacuum to produce a lipid film adhering to the vessel;
    (c) reconstituting the lipid film in a non-aqueous and/or dehydrated solvent in a volume that is a fraction of an intended final volume to form a non-aqueous mixture of the retinoid and phospholipid;
    (d) adding water in at least two steps to the solution of (c) with sonication of the solution after each step, wherein the volume of water added at each step is the same as, or greater than, the volume added in the previous step, to produce a lipid dispersion in water that comprises the retinoid; and
    (e) homogenizing the suspension of (d) under conditions sufficient to produce a population of lipid particles with an average diameter of less than about 1000 nm.

19. The method of claim 18 wherein the neutral retinoid is HPR.

20. The method of claim 18 wherein, in addition to the retinoid, a second, lipid soluble agent to be used together with the retinoid in a pharmaceutical composition or method is dissolved in said solvent or solvent mixture of step (a) and incorporated into the lipid film.

21. An emulsion composition of a neutral retinoid comprising a hydrophilic and hydrophobic phase, and comprising in combination:
    (a) between about 4 and about 75 mg/ml of a neutral retinoid;
    (b) a plant lecithin or phospholipid components from said lecithin as a hydrophobic phase present in an amount that confers upon the emulsion the following properties:
        (i) the hydrophobic phase is dispersed in the hydrophilic phase as particles having diameters in the range of about 100 nm to about 5000 nm;
        (ii) the composition is filterable through polycarbonate filters with pore sizes ranging between 0.2 µm and 5 µm without substantially altering the amount of active retinoid or the particle size range;
    (c) ethanol at a concentration of between about 0.01 to about 10% v/v; and
    (d) glycerin at a concentration of between about 5 and about 100 mg/ml.

22. A pharmaceutical composition comprising the emulsion composition of claim 21 for intravenous or other parenteral administration to a human subject in need thereof, which pharmaceutical composition is free of non-ionic surfactants, detergents, polyoxylated compounds, alkoxylated oils or any animal-derived substance known to be allergenic or to induce an anaphylactic reaction when administered to a human.

23. The emulsion composition of claim 21 wherein the retinoid is HPR.

24. A topical nanoparticle composition comprising the nanoparticle composition of claim 1 in a topical formulation.

25. A pharmaceutical composition comprising the emulsion composition of claim 23 suitable for intravenous and other parenteral administration to a human subject in need thereof, which pharmaceutical composition is free of non-ionic surfactants, detergents, polyoxylated compounds, alkoxylated oils or any animal substance known to be allergenic or to induce an anaphylactic reaction when administered to a human.

26. The lipid nanoparticle composition of claim 1 wherein the neutral retinoid is a synthetic amide, alcohol or ester of a retinoic acid.

27. The lipid nanoparticle composition of claim 1 wherein the nanoparticles have a surface charge characterized by a zeta potential of between about −36 millivolts and about −11 millivolts.

28. The lipid nanoparticle composition of claim 1 wherein the nanoparticles have a surface charge characterized by a zeta potential of between −11 millivolts and −4.6 millivolts.

29. The lipid nanoparticle composition of claim 9 wherein the two of said phospholipids are DMPG and DMPC which contribute to control of the surface charge.

30. The lipid nanoparticle composition of claim 29 wherein the DMPC and DMPG are present in a DMPC:DMPG ratio of between about 3 and about 100.

31. The lipid nanoparticle composition of claim 14 wherein the concentration of DMPC and DMPG are in the range of:
    (d) 1.4 to 20 mg/ml DMPC;
    (e) 0.76 to 10 mg/ml DMPG.

32. The lipid nanoparticle composition of claim 16, wherein the concentration of DMPC and DMPG are in the range of:
    (d) 1.4 to 20 mg/ml DMPC;
    (e) 0.76 to 10 mg/ml DMPG.

33. The topical nanoparticle composition of claim 24 wherein the retinoid is HPR.

34. The method of any of claim 18 wherein in step (d), the water is added in at least five steps.

35. The method of claim 19 wherein steps (a)-(e) are carried out under aseptic or sterile conditions.

36. The method of claim 18 wherein the lipid nanoparticles produced in step (e) are filtered through a polycarbonate filter with a pore size of about 0.2 μm to eliminate larger vesicles that are undesirable for intravenous injection into humans.

* * * * *